US011925419B2

(12) United States Patent
Zhang et al.

(10) Patent No.: US 11,925,419 B2
(45) Date of Patent: Mar. 12, 2024

(54) SYSTEMS AND METHODS FOR POSITION DETERMINATION

(71) Applicant: SHANGHAI UNITED IMAGING HEALTHCARE CO., LTD., Shanghai (CN)

(72) Inventors: Xinyue Zhang, Shanghai (CN); Tuoyu Cao, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 17/452,577

(22) Filed: Oct. 28, 2021

(65) Prior Publication Data

US 2022/0202499 A1 Jun. 30, 2022

(30) Foreign Application Priority Data

Dec. 30, 2020 (CN) .......................... 202011628121.2
Dec. 30, 2020 (CN) .......................... 202011628122.7

(51) Int. Cl.
*A61B 34/20* (2016.01)
*A61B 5/00* (2006.01)
(Continued)

(52) U.S. Cl.
CPC ............ *A61B 34/20* (2016.02); *A61B 5/0035* (2013.01); *A61B 5/055* (2013.01); *A61B 5/062* (2013.01);
(Continued)

(58) Field of Classification Search
CPC ....... A61B 34/20; A61B 5/0035; A61B 5/055; A61B 5/062; A61B 5/721; A61B 2034/2051; G01R 33/032
See application file for complete search history.

(56) References Cited

U.S. PATENT DOCUMENTS 6,396,268 B1 5/2002 Hinks et al.
2004/0167393 A1 8/2004 Solar et al.
(Continued)

FOREIGN PATENT DOCUMENTS

CN 101019765 A 8/2007
CN 104771167 A 7/2015
(Continued)

OTHER PUBLICATIONS

Simon Gross et al., Dynamic Nuclear Magnetic Resonance Field Sensing with Part-Per-Trillion Resolution, Nature Communications, 2016, 7 pages.
(Continued)

*Primary Examiner* — Katherine L Fernandez
*Assistant Examiner* — Brooke Lyn Klein
(74) *Attorney, Agent, or Firm* — METIS IP LLC

(57) ABSTRACT

The present disclosure is related to systems and methods for position determination. The method includes obtaining, via a plurality of sensors, real-time target magnetic field information of a target subject. The plurality of sensors may be configured on the target subject. The target subject may be located in a reference magnetic field in a medical system. The method includes determining real-time target position information of the target subject based on the real-time target magnetic field information of the target subject and magnetic field distribution information of the reference magnetic field in the medical system.

19 Claims, 9 Drawing Sheets

(51) Int. Cl.
*A61B 5/055* (2006.01)
*A61B 5/06* (2006.01)
*G01R 33/032* (2006.01)

(52) U.S. Cl.
CPC ............ *A61B 5/721* (2013.01); *G01R 33/032* (2013.01); *A61B 2034/2051* (2016.02)

(56) References Cited

U.S. PATENT DOCUMENTS

| | | | |
|---|---|---|---|
| 2006/0004281 A1* | 1/2006 | Saracen | A61B 5/1127 600/414 |
| 2010/0142670 A1* | 6/2010 | Saito | A61B 6/032 378/8 |
| 2011/0080167 A1 | 4/2011 | Kannengisser et al. | |
| 2013/0049756 A1* | 2/2013 | Ernst | G01R 33/56509 324/322 |
| 2016/0073980 A1 | 3/2016 | Weng et al. | |
| 2016/0161429 A1 | 6/2016 | Englund et al. | |
| 2016/0169838 A1 | 6/2016 | Nagarkar et al. | |
| 2016/0213430 A1 | 7/2016 | Mucha | |
| 2019/0038177 A1 | 2/2019 | Duek | |
| 2019/0178967 A1 | 6/2019 | Guo et al. | |
| 2019/0336014 A1 | 11/2019 | Peeters et al. | |
| 2020/0132785 A1* | 4/2020 | Yoshii | G01R 33/02 |
| 2020/0284863 A1 | 9/2020 | Leussler et al. | |

FOREIGN PATENT DOCUMENTS

| | | |
|---|---|---|
| CN | 107356820 A | 11/2017 |
| CN | 107374719 A | 11/2017 |
| CN | 109270478 A | 1/2019 |
| CN | 109443337 A | 3/2019 |
| CN | 109975727 A | 7/2019 |
| CN | 111650233 A | 9/2020 |
| CN | 111650543 A | 9/2020 |
| CN | 111693914 A | 9/2020 |
| CN | 112798995 A | 5/2021 |
| DE | 102017205710 A1 | 10/2018 |

OTHER PUBLICATIONS

First Office Action in Chinese Application No. 202011628122.7 dated Oct. 22, 2021, 19 pages.
First Office Action in Chinese Application No. 202011631231.4 dated Mar. 31, 2022, 21 pages.

* cited by examiner

SYSTEMS AND METHODS FOR POSITION DETERMINATION

CROSS-REFERENCE TO RELATED APPLICATIONS

This application claims priority of Chinese Patent Application No. 202011628121.2, filed on Dec. 30, 2020, and Chinese Patent Application No. 202011628122.7, filed on Dec. 30, 2020, the contents of each of which are hereby incorporated by reference.

TECHNICAL FIELD

This disclosure generally relates to a medical system, and more particularly, relates to systems and methods for determining a position of a subject in the medical system.

BACKGROUND

Medical systems, such as an MRI device, a PET device, a CT device are widely used for creating images of the interior of a patient for, e.g., diagnosis and/or treatment purposes. A motion (e.g., a posture motion, a physiological motion) of a scan region of a patient during a scan may affect imaging quality by causing, for example, motion artifacts in a resulting image, which in turn may hinder an accurate detection, localization, and/or quantification of a possible lesion (e.g., a tumor). Accurate motion detection of the scan region of the patient during the scan may improve the quality of the image generated based on the scan. In addition, in a medical operation (e.g., a puncture surgery, a minimally invasive surgery), one or more operating elements (e.g., a puncture needle) may be used to treat a patient. Accurate positioning of the operating element may improve the effectiveness and quality of the medical operation. Therefore, it is desirable to provide effective systems or methods for position determination in the medical system.

SUMMARY

According to an aspect of the present disclosure, a method may be implemented on a computing device having one or more processors and one or more storage devices. The method may include obtaining, via a plurality of sensors, real-time target magnetic field information of a target subject. The plurality of sensors may be configured on the target subject. The target subject may be located in a reference magnetic field in a medical system. The method may include determining real-time target position information of the target subject based on the real-time target magnetic field information of the target subject and magnetic field distribution information of the reference magnetic field in the medical system.

In some embodiments, the plurality of sensors may include a diamond nitrogen-vacancy (NV) center sensor. The method may include obtaining information of at least one pair of magnetic resonance peaks of a diamond NV center in the diamond NV center sensor. The at least one pair of magnetic resonance peaks of the diamond NV center may be obtained by splitting a total magnetic resonance peak of the diamond NV center via the reference magnetic field. Each pair of the at least one pair of magnetic resonance peaks may correspond to a crystal axis direction of the diamond NV center. The method may include obtaining the real-time target magnetic field information of the target subject based on the information of the at least one pair of magnetic resonance peaks of the diamond NV center.

In some embodiments, the method may include, for each pair of the at least one pair of magnetic resonance peaks of the diamond NV center, determining candidate magnetic field information related to the corresponding crystal axis direction of the diamond NV center based on the information of the pair of magnetic resonance peaks. The method may include determining the real-time target magnetic field information based on the candidate magnetic field information of the diamond NV center and a coordinate transformation relationship between a crystal coordinate system of the diamond NV center and a magnetic field coordinate system of the reference magnetic field.

In some embodiments, the target subject may be a scan region of a patient. The method may include obtaining, via the plurality of sensors, first magnetic field information of the target subject corresponding to a first time point. The method may include obtaining, via the plurality of sensors, second magnetic field information of the target subject corresponding to a second time point, wherein the second time point is different from the first time point.

In some embodiments, the real-time target position information of the target subject may include motion information of the target subject between the first time point and the second time point. The method may include determining first position information of the target subject corresponding to the first time point based on the first magnetic field information of the target subject and the magnetic field distribution information of the reference magnetic field. The method may include determining second position information of the target subject corresponding to the second time point based on the second magnetic field information of the target subject and the magnetic field distribution information of the reference magnetic field. The method may include determining the motion information of the target subject between the first time point and the second time point based on the first position information and the second position information.

In some embodiments, the method may include causing a medical device to scan the target subject based on the motion information of the target subject.

In some embodiments, the medical device may be a magnetic resonance imaging (MRI) device. The method may include determining correction information based on the motion information of the target subject. The method may include obtaining an MRI image of the target subject by causing the MRI device to scan the target subject based on the correction information.

In some embodiments, the correction information may include at least one of gradient correction information or radio frequency correction information.

In some embodiments, the method may include causing a gradient component of the MRI device to generate a gradient magnetic field based on the gradient correction information. The method may include causing a radio frequency component of the MRI device to obtain an MRI signal of the target subject based on the radio frequency correction information. The method may include obtaining spatial encoding information based on the gradient magnetic field. The method may include obtaining the MRI image of the target subject by processing the MRI signal based on the spatial encoding information.

In some embodiments, the medical device may include at least one of a positron emission tomography (PET) device, a computed tomography (CT) device, an X-ray imaging device, or a radiation therapy (RT) device. The reference magnetic field may be generated by an external magnetic field generating device.

In some embodiments, the target subject may be an operating element. The method may include obtaining reference position information of a reference subject in the medical system. The method may include obtaining first relative position information between a candidate subject and the reference subject. The method may include determining second relative position information between the target subject and the reference subject based on the real-time target position information of the target subject and the reference position information of the reference subject. The method may include determining third relative position information between the target subject and the candidate subject based on the first relative position information and the second relative position information.

In some embodiments, the method may include displaying an image reflecting the third relative position information.

According to an aspect of the present disclosure, a system may include at least one storage device storing a set of instructions, and at least one processor in communication with the at least one storage device. When executing the stored set of instructions, the at least one processor may cause the system to perform a method. The method may include obtaining, via a plurality of sensors, real-time target magnetic field information of a target subject. The plurality of sensors may be configured on the target subject. The target subject may be located in a reference magnetic field in a medical system. The method may include determining real-time target position information of the target subject based on the real-time target magnetic field information of the target subject and magnetic field distribution information of the reference magnetic field in the medical system.

According to still another aspect of the present disclosure, a non-transitory computer readable medium may include at least one set of instructions. When executed by at least one processor of a computing device, the at least one set of instructions may cause the at least one processor to effectuate a method. The method may include obtaining, via a plurality of sensors, real-time target magnetic field information of a target subject. The plurality of sensors may be configured on the target subject. The target subject may be located in a reference magnetic field in a medical system. The method may include determining real-time target position information of the target subject based on the real-time target magnetic field information of the target subject and magnetic field distribution information of the reference magnetic field in the medical system.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
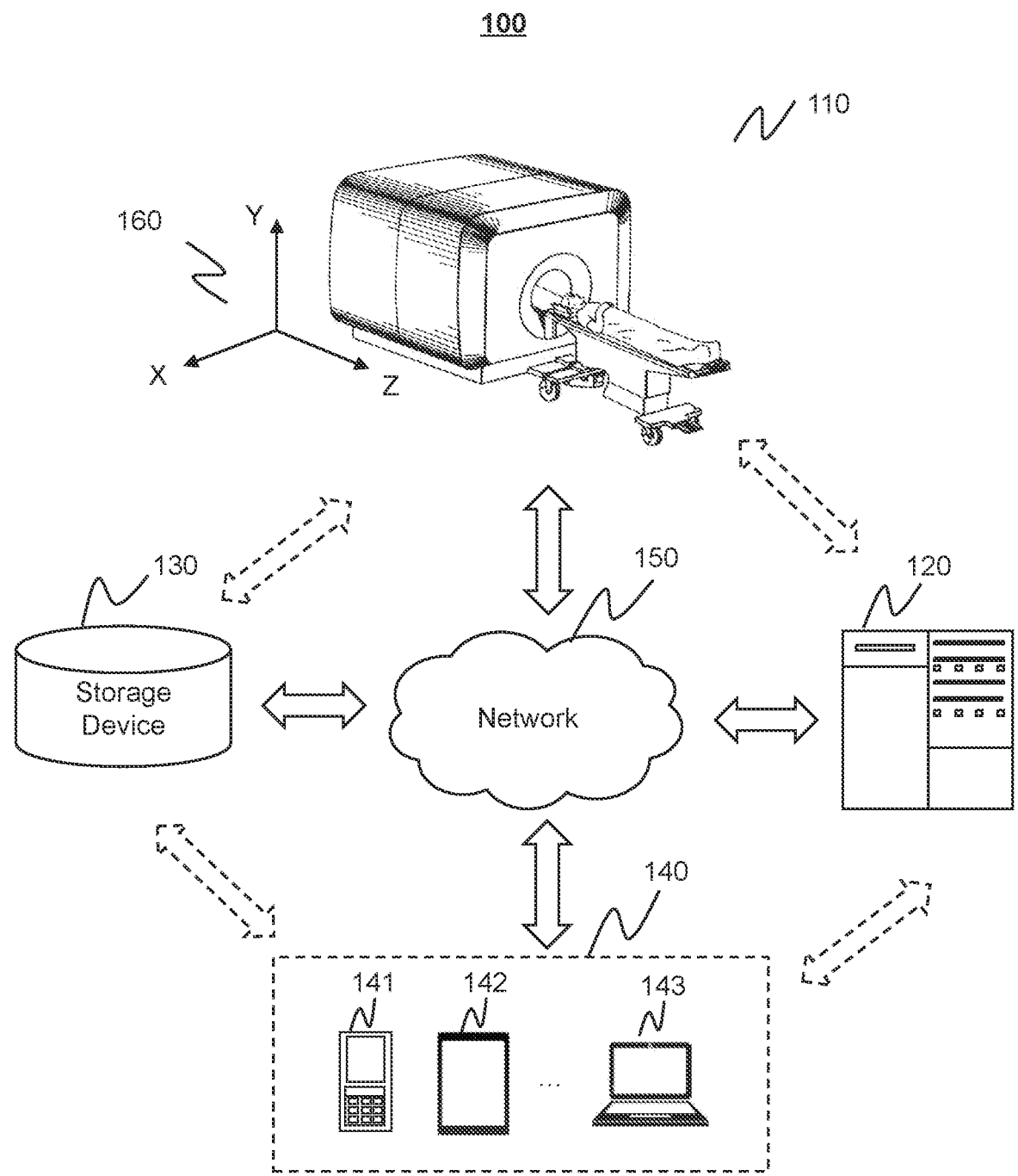
FIG. 1 is a schematic diagram illustrating an exemplary medical system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, the term "exemplary" is intended to refer to an example or illustration.

It will be understood that the terms "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

The term "pixel" and "voxel" in the present disclosure are used interchangeably to refer to an element in an image. The term "image" in the present disclosure is used to refer to images of various forms, including a 2-dimensional image, a 3-dimensional image, a 4-dimensional image, etc.

Spatial and functional relationships between elements are described using various terms, including "connected," "attached," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent," etc.).

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood the operations of the flowcharts may be implemented not in order. Conversely, the operations may be implemented in inverted order, or simultaneously. Moreover, one or more other operations may be added to the flowcharts. One or more operations may be removed from the flowcharts.

Moreover, while the systems and methods disclosed in the present disclosure are described primarily regarding position determination in a magnetic resonance imaging (MRI) system. It should be understood that this is only for illustration purposes. The systems and methods of the present disclosure may be applied to any other kind of medical system. In some embodiments, the medical system may include a single modality system and/or a multi-modality system. The single modality system may include, for example, an MRI system, a positron emission tomography (PET) system, a computed tomography (CT) system, a single photon emission computed tomography (SPECT) device, a radiotherapy (RT) device or the like. The multi-modality system may include, for example, an MRI-CT system, a PET-MRI system, a SPECT-MRI system, a digital subtraction angiography (DSA)-MRI system, a PET-CT system, or the like.

A scan process (e.g., an MRI scan process) usually takes a relatively long time (e.g., 10 to 30 minutes). During the scan process, a patient to be scanned may need to remain as still as possible. A motion (e.g., a posture motion, a physiological motion) of the patient during the scan process may cause resolution degradation and/or introduce artifacts in a medical image that affect diagnoses and/or treatment performed on the basis of the medical image. In addition, the motion during the scan process may cause unnecessary radiation to the patient, which may be harmful to the patient. In some embodiments, one or more post-processing algorithms may be used to process scan data to correct motion artifacts. In some embodiments, the motion of the patient may be monitored using an imaging device (e.g., a camera) during the scan process. Motion information of the patient may be determined based on image data obtained by the imaging device. The scan data of the patient may be corrected based on the motion information. However, it may take a large amount of image to determine the motion information of the patient, which may increase the operating load on the medical system, and reduce the efficiency of the medical system.

In addition, in a medical operation (e.g., a puncture surgery, a minimally invasive surgery), one or more operating elements (e.g., a puncture needle) may be used to treat a patient. An accurate positioning of the operating element may improve the effectiveness of the medical operation. For example, position information of the operating element and anatomical information of the patient may be displayed for monitoring and/or obtaining guidance for the medical operation. Traditionally, an optical-based positioning system or an electromagnetic positioning system may be used to determine the position information of the operating element during the medical operation. For example, a three-dimensional (3D) model reflecting the anatomical structure of a patient may be reconstructed based on a medical image (e.g., a CT image, an MRI image) of the patient. A user, e.g., a doctor, may observe tissue structure around the lesion of the patient based on the 3D model, and determine a surgical plan before the medical operation. During the medical operation, an infrared locator (or an electromagnetic locator) configured above a scanning table may track and locate the operating element, or a portion thereof; an infrared locator (or an electromagnetic locator) configured on the patient may track and locate the patient, or a portion thereof. The relative position information between the patient and the operating element may be determined and displayed to the user in (substantially) real time for monitoring and/or obtaining guidance for the medical operation. As used herein, "substantially," when used to describe a term (e.g., real time), indicates that the deviation from the term is below a threshold. The threshold may be an absolute number or a relative number with respect to a reference number. For instance, with respect to the phrase "substantially real time," the threshold may be an absolute number (e.g., 5 seconds, 2 seconds, 1 second, 0.5 seconds, etc.) or a relative number with respect to a reference number (e.g., 20%, 10%, 5%, 1%, etc., of the duration of a cardiac cycle). However, when the medical operation is performed inside the patient, the operating element cannot be accurately positioned using the optical-based positioning system. In addition, due to the influence of magnetic fields generated by an MRI device, the accuracy and reliability for positioning the operating element using the electromagnetic positioning system may be relatively low.

An aspect of the present disclosure relates to a system and method for determining target position information of a scan region of a patient. A processing device may obtain, via a plurality of sensors (e.g., a plurality of diamond nitrogen-vacancy (NV) center sensors), real-time target magnetic field information of the scan region. The plurality of diamond NV center sensors may be configured on different positions of the scan region of the patient (e.g., arranged around the scan region). A portion of the scan region may be located in a reference magnetic field (e.g., a main magnetic field, a gradient field) in a medical system (e.g., an MRI system). The processing device may determine real-time target position information (e.g., motion information) of the scan region based on the real-time target magnetic field information of the scan region and magnetic field distribution information of the reference magnetic field in the medical system. Accordingly, a medical device may be controlled to scan the scan region based on the real-time target position information of the scan region, which may reduce motion artifacts in a medical image of the scan region, and improve the quality of the medical image.

Another aspect of the present disclosure relates to a system and method for determining target position information of an operating element. A processing device may obtain, via at least one sensor (e.g., at least one diamond NV center sensor), real-time target magnetic field information of the operating element. The diamond NV center sensor may be configured on the operating element. A portion of the operating element may be located in a reference magnetic field (e.g., a main magnetic field, a gradient field) in a medical system (e.g., an MRI system). The processing device may determine real-time target position information of the operating element based on the real-time target magnetic field information of the operating element and magnetic field distribution information of the reference magnetic field in the medical system. Accordingly, an image illustrating relative position information between a patient and the operating element may be displayed to a user (e.g., a doctor) for guidance in a medical operation, which may improve the efficiency and accuracy of the medical operation.

FIG. 1 is a schematic diagram illustrating an exemplary medical system according to some embodiments of the present disclosure. As illustrated, a medical system 100 may include a medical device 110, a processing device 120, a storage device 130, a terminal 140, and a network 150. The components of the medical system 100 may be connected in one or more of various ways. Merely by way of example, as illustrated in FIG. 1, the medical device 110 may be connected to the processing device 120 directly as indicated by the bi-directional arrow in dotted lines linking the medical device 110 and the processing device 120, or through the network 150. As another example, the storage device 130 may be connected to the medical device 110 directly as indicated by the bi-directional arrow in dotted lines linking the medical device 110 and the storage device 130, or through the network 150. As still another example, the terminal 140 may be connected to the processing device 120 directly as indicated by the bi-directional arrow in dotted lines linking the terminal 140 and the processing device 120, or through the network 150.

The medical device 110 may generate or provide image data by scanning an object or at least a part of the object and/or perform a treatment (e.g., radiotherapy) on the at least one part of the object. In some embodiments, the medical device 110 may include a single-modality device. The single-modality device may include, for example, an MRI device, a CT device, a PET device, an X-ray imaging device, a radiation therapy or radiotherapy (RT) device, or the like. In some embodiments, the medical device 110 may include a multi-modality device. The multi-modality scanner may include a PET-CT device, a PET-MRI device, a CT-MRI device, or the like. The multi-modality scanner may perform multi-modality imaging simultaneously. For example, the PET-CT device may generate structural X-ray CT image data and functional PET image data simultaneously in a single scan. The PET-MRI device may generate MRI data and PET data simultaneously in a single scan. In some embodiments, the medical device 110 may include an image-guided radiotherapy (IGRT) device. For example, the IGRT device may include a PET-RT device, or an MRI-RT device, etc.

Merely by way of example, the medical device 110 may be an MRI device configured to scan an object (or a part of the object) to acquire image data, such as echo signals (or MRI signals) associated with the object. For example, the medical device 110 may detect a plurality of echo signals by applying an MRI pulse sequence on the object. In some embodiments, the medical device 110 may include, for example, a main magnet, a gradient coil (or also referred to as a spatial encoding coil), a radio frequency (RF) coil, etc., as described in connection with FIG. 2. In some embodiments, the medical device 110 may be a permanent magnet MRI scanner, a superconducting electromagnet MRI scanner, a resistive electromagnet MRI scanner, etc., according to types of the main magnet. In some embodiments, the medical device 110 may be a high-field MRI scanner, a mid-field MRI scanner, a low-field MRI scanner, etc., according to the intensity of the magnetic field.

The object may be biological or non-biological. For example, the object may include a patient, a man-made object, etc. As another example, the object may include a specific portion, an organ, and/or tissue of the patient. Specifically, the object may include the head, the neck, the thorax, the heart, the stomach, a blood vessel, soft tissue, a tumor, or the like, or any combination thereof. In some embodiments the object may be a target subject as described elsewhere in the present disclosure.

In some embodiments, a coordinate system 160 may be provided for the medical system 100. For illustration purposes, the coordinate system 160 may include an X-axis, a Y-axis, and a Z-axis. The X-axis and the Z-axis shown in FIG. 1 may be horizontal, and the Y-axis may be vertical. As illustrated, a positive X direction along the X-axis may be from the right side to the left side of the medical device 110 viewed from the direction facing the front of the medical device 110; a positive Y direction along the Y-axis may be from the lower part (or from the floor where the medical device 110 stands) to the upper part of the medical device 110; and a positive Z direction along the Z-axis may be the direction in which the object is moved out of a scanning channel (or referred to as a bore) of the medical device 110.

It should be noted that the provided coordinate system 160 is illustrative, and not intended to limit the scope of the present disclosure. For example, the coordinate system 160 may only include two axes (e.g., the X-axis and the Y-axis). As another example, the coordinate system 160 may include four axes. In addition, although the following descriptions discuss through various examples to determine a position of an entity by determining a coordinate of an entity in a certain coordinate system, it should be understood that the position of the entity may be determined by determining a coordinate of the entity in another coordinate system (e.g., a coordinate system that has a known transformation relationship with the certain coordinate system). For the convenience of descriptions, coordinates of an entity along an X-axis, a Y-axis, and a Z-axis in a coordinate system are also referred to as X-coordinates, Y-coordinates, and Z-coordinates of the entity in the coordinate system, respectively.

In some embodiments, the medical device 110 may be directed to select an anatomical slice of the object along a slice selection direction and scan the anatomical slice to acquire a plurality of echo signals from the slice. During the scan, spatial encoding within the slice may be implemented by spatial encoding coils (e.g., an X coil and a Y coil) along a phase encoding direction and a frequency encoding direction. The echo signals may be sampled and the corresponding sampled data may be stored into a K-space matrix for image reconstruction. For illustration purposes, the slice-selection direction herein may correspond to the Z direction defined by the coordinate system 160 and a Kz direction in K-space; the phase-encoding direction may correspond to the Y direction defined by the coordinate system 160 and a Ky direction in K-space; and the frequency-encoding direction may correspond to the X direction defined by the coordinate system 160 and a Kx direction in K-space. It should be noted that the slice-selection direction, the phase-encoding direction, and the frequency-encoding direction may be modified according to actual needs, and the modification may do not depart the scope of the present disclosure. More description of the medical device 110 may be found elsewhere in the present disclosure. See, e.g., FIG. 2 and the description thereof.

The processing device 120 may process data and/or information obtained from the medical device 110, the storage device 130, and/or the terminal(s) 140. For example, the processing device 120 may obtain, via a plurality of sensors (e.g., a plurality of diamond NV center sensors), real-time target magnetic field information of a target subject (e.g., a scan region of a patient, an operating element). The plurality of sensors (e.g., the plurality of diamond NV center sensors) may be configured on the target subject. As another example, the processing device 120 may determine real-time target position information of a target subject based on real-time target magnetic field information of the target subject and magnetic field distribution information of a reference magnetic field in the medical system 100. In some embodiments, the processing device 120 may be a single server or a server group. The server group may be centralized or distributed. In some embodiments, the processing device 120 may be local or remote. For example, the processing device 120 may access information and/or data from the medical device 110, the storage device 130, and/or the terminal(s) 140 via the network 150. As another example, the processing device 120 may be directly connected to the medical device 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be part of the terminal 140. In some embodiments, the processing device 120 may be part of the medical device 110.

The storage device 130 may store data, instructions, and/or any other information. In some embodiments, the storage device 130 may store data obtained from the medical device 110, the processing device 120, and/or the terminal(s) 140. The data may include image data acquired by the processing device 120, algorithms and/or models for processing the image data, etc. For example, the storage device 130 may store target magnetic field information of a target subject obtained from at least one diamond NV center sensor. As another example, the storage device 130 may store magnetic field distribution information of a reference magnetic field in the medical system 100. As still another example, the storage device 130 may store target position information of a target subject determined by the processing device 120. In some embodiments, the storage device 130 may store data and/or instructions that the processing device 120 and/or the terminal 140 may execute or use to perform exemplary methods described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random-access memory (RAM). Exemplary RAM may include a dynamic RAM (DRAM), a double date rate synchronous dynamic RAM (DDR SDRAM), a fast page mode dynamic RAM (FPMDRAM), an extended date out dynamic RAM (EDODRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), an electrically alterable ROM (EAROM), a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the medical system 100 (e.g., the processing device 120, the terminal(s) 140). One or more components in the medical system 100 may access the data or instructions stored in the storage device 130 via the network 150. In some embodiments, the storage device 130 may be integrated into the medical device 110.

The terminal(s) 140 may be connected to and/or communicate with the medical device 110, the processing device 120, and/or the storage device 130. In some embodiments, the terminal 140 may include a mobile device 141, a tablet computer 142, a laptop computer 143, or the like, or any combination thereof. For example, the mobile device 141 may include a mobile phone, a personal digital assistant (PDA), a gaming device, a navigation device, a point of sale (POS) device, a laptop, a tablet computer, a desktop, or the like, or any combination thereof. In some embodiments, the terminal 140 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. Other types of the input device may include a cursor control device, such as a mouse, a trackball, or cursor direction keys, etc. The output device may include a display, a printer, or the like, or any combination thereof.

The network 150 may include any suitable network that can facilitate the exchange of information and/or data for the medical system 100. In some embodiments, one or more components of the medical system 100 (e.g., the medical device 110, the processing device 120, the storage device 130, the terminal(s) 140, etc.) may communicate information and/or data with one or more other components of the medical system 100 via the network 150. For example, the processing device 120 and/or the terminal 140 may obtain target magnetic field information of a target subject from at least one diamond NV center sensor via the network 150. As another example, the processing device 120 and/or the terminal 140 may obtain information stored in the storage device 130 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a long term evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the medical system 100 may be connected to the network 150 to exchange data and/or information.

Figure 2:
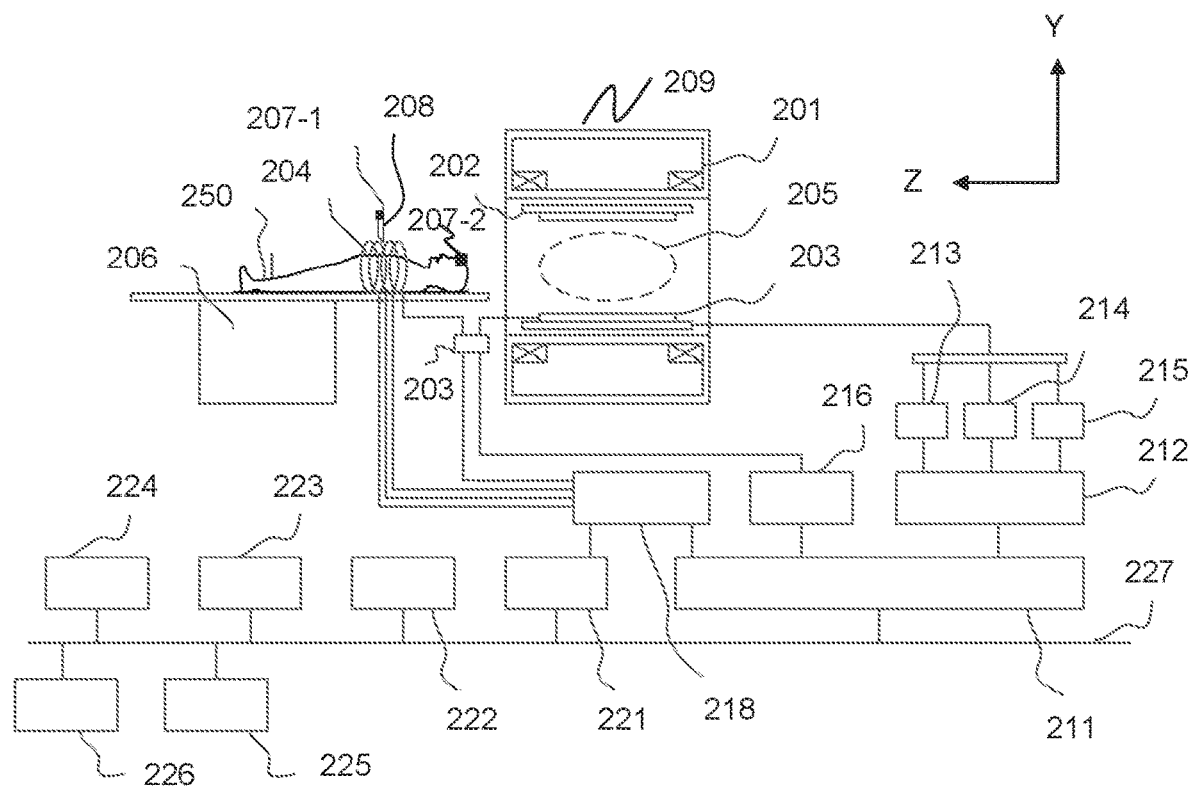
FIG. 2 is a schematic diagram illustrating an exemplary medical system according to some embodiments of the present disclosure.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure. In some embodiments, the medical system 100 may include one or more other components. For example, the medical system 100 may include a diamond NV center sensor (e.g., a diamond NV center sensor 207-1 and a diamond NV center sensor 207-2 as illustrated in FIG. 2). As another example, the medical system 100 may include an external magnetic field generating device (not shown in FIG. 1). The external magnetic field generating device may be configured to generate a magnetic field in the medical system 100. For example, the external magnetic field generating device may generate a first magnetic field along the X-axis direction, a second magnetic field along the Y-axis direction, and a third magnetic field along the Z-axis direction.

FIG. 2 is a schematic diagram illustrating an exemplary medical system according to some embodiments of the present disclosure. As shown in FIG. 2, a medical system 200 may include an MRI device, a computing device, and at least one diamond NV center sensor (e.g., the diamond NV center sensor 207-1, the diamond NV center sensor 207-2).

The diamond NV center sensor may be configured to detect target magnetic field information of a target subject before, during, and/or after a scan (e.g., an MRI scan) of the target subject. The target magnetic field information of the target subject may be used to determine target position information of the target subject. The diamond NV center sensor refers to a sensor based on a diamond NV center. The NV center is a point defect in the diamond lattice. The NV center includes a nearest-neighbor pair of a nitrogen atom, which substitutes for a carbon atom, and a lattice vacancy. The diamond NV center sensor may be used within a relatively wide temperature range (e.g., at room temperatures). The diamond NV center sensor may be used within a magnetic field strength range of 0.06 T~10 T. The magnetic field information measurement based on the diamond NV center sensor may have a relatively high spatial resolution (e.g., a nano-scale spatial resolution) and a relatively high magnetic sensitivity (e.g., a microtesla-scale magnetic sensitivity). The diamond NV center sensor may impose substantially no disturbance to magnetic fields generated by the MRI device in the medical system 200. In addition, due to an atomic size of the diamond NV center, the diamond NV center sensor may have a small size (e.g., 1 mm$^3$) so as to be placed close to the target subject in a nanometer level. The diamond NV center sensor may measure spins of a single electron and/or a single nuclear, and the diamond NV center may achieve a single-molecule nuclear magnetic resonance and a single-molecule paramagnetic resonance in an MRI system.

In some embodiments, the at least one diamond NV center sensor may be configured on the target subject. The target subject may include a scan region of a patient 250 and/or an operating element 208. As used herein, a scan region of a patient refers to a region (e.g., a specific portion, an organ, tissue) of the patient to be scanned by a medical device (e.g., the MRI device). For example, the scan region may include the head, the thorax, the abdomen, or the like, of the patient. The operating element 208 may be used to perform a medical operation (e.g., a puncture surgery, a minimally invasive surgery) on the patient 250. For example, the operating element 208 may include a mechanical cutter (e.g., a scalpel, a lancet, a trocar, a rongeur), a pair of surgical scissors (e.g., tissue scissors, stitch scissors), a pair of forceps (e.g., thumb tweezers, locking forceps), a needle driver, a needle, a retractor, a suction tip, a probe, or the like, or any combination thereof.

In some embodiments, the diamond NV center sensor may be configured at one of various suitable positions of the target subject. For example, if the scan region is the head of the patient 250, one or more diamond NV center sensors 207-2 may be disposed on the nose bridge and/or the forehead of the patient 250 to obtain the target position information (e.g., motion information) of the head during a scan process in (substantially) real time. As another example, if the scan region is the chest of the patient, one or more diamond NV center sensors 207-2 may be disposed on an area near the heart of the patient to obtain the target position information (e.g., motion information) of the chest during the scan process in (substantially) real time.

As still another example, one or more diamond NV center sensors 207-1 may be mounted on an end and/or a side surface of the operating element 208 to obtain target position information of the operating element 208 during a medical operation in (substantially) real time. For illustration purposes, a puncture needle may have a first end and a second end. A diamond NV center sensor may be mounted on the first end of the puncture needle. The diamond NV center sensor may obtain target magnetic field information of the first end of the puncture needle. The target position information of the first end of the puncture needle may be determined based on the target magnetic field information of the first end of the puncture needle. Target position information of the second end of the puncture needle may be determined based on the target position information of the first end and a known shape of the puncture needle (e.g., a distance between the first end and the second end).

The MRI device may be configured to scan the patient 250 (or a part of the patient 250) to acquire image data, such as echo signals (or MRI signals) associated with the patient 250. In some embodiments, the MRI device may include a main magnet 201, gradient coils 202, RF coils (not shown in FIG. 2), a gantry 209, and a scanning table 206.

The main magnet 201 may be located inside the gantry 209. The main magnet 201 may generate a first magnetic field (or referred to as a main magnetic field) that may be applied to the patient 250 exposed inside the field. The magnetic field strength of the main magnetic field may be 0.2 Tesla, 0.5 Tesla, 1.0 Tesla, 1.5 Tesla, 3.0 Tesla, etc. The main magnet 201 may include a resistive magnet or a superconductive magnet that both need a power supply (not shown) for operation. Alternatively, the main magnet 201 may include a permanent magnet. The main magnet 201 may include a bore that the subject is placed within. The bore may form a field of view (FOV) of the MRI device. As used herein, an FOV of a medical device (e.g., the MRI device) refers to an area or region scanned by the medical device during a scan of an object (e.g., the patient 250). The main magnet 201 may also control the homogeneity of the generated main magnetic field. Some shim coils may be in the main magnet 201. The shim coils placed in the gap of the main magnet 201 may compensate for the inhomogeneity of the magnetic field of the main magnet 201. The shim coils may be energized by a shim power supply.

In some embodiments, the patient 250 may be positioned in a region 205 where the main magnetic field is relatively uniformly distributed. For example, the patient 250 may be positioned on the scanning table 206 during the MRI scan. The scanning table 206 may move in various directions to position the patient 250 in the region 205.

The gradient coils 202 may be located inside the main magnet 201. The gradient coils 202 may generate a second magnetic field (or referred to as a gradient field, including gradient fields Gx, Gy, and Gz). The gradient field may be superimposed on the main magnetic field generated by the main magnet 201 and distort the main field so that the magnetic orientations of the protons of an object may vary as a function of their positions inside the gradient field, thereby encoding spatial information into echo signals generated by the region of the object being imaged. The gradient coils 202 may include X coils (e.g., configured to generate the gradient field Gx corresponding to the X direction), Y coils (e.g., configured to generate the gradient field Gy corresponding to the Y direction), and/or Z coils (e.g., configured to generate the gradient field Gz corresponding to the Z direction) (not shown in FIG. 2). In some embodiments, the Z coils may be designed based on circular (Maxwell) coils, while the X coils and the Y coils may be designed on the basis of the saddle (Golay) coil configuration. The three sets of coils may generate three different magnetic fields that are used for position encoding.

In some embodiments, the X direction may be designated as a frequency encoding direction, while the Y direction may be designated as a phase encoding direction. In some embodiments, Gx may be used for frequency encoding or signal readout, generally referred to as frequency encoding gradient or readout gradient. In some embodiments, Gy may be used for phase encoding, generally referred to as phase encoding gradient. In some embodiments, Gz may be used for slice selection for obtaining 2D k-space data. In some embodiments, Gz may be used for phase encoding for obtaining 3D k-space data.

The gradient coils 202 may allow spatial encoding of echo signals for image construction. The gradient coils 202 may be connected with one or more of an X gradient amplifier 213, a Y gradient amplifier 214, or a Z gradient amplifier 215. One or more of the three amplifiers may be connected to a waveform generator. The waveform generator may generate gradient waveforms that are applied to the X gradient amplifier 213, the Y gradient amplifier 214, and/or the Z gradient amplifier 215. An amplifier may amplify a waveform. An amplified waveform may be applied to one of the coils in the gradient coils 202 to generate a magnetic field in the X-axis, the Y-axis, or the Z-axis, respectively. The gradient coils 202 may be designed for either a close-bore MRI scanner or an open-bore MRI scanner. For example, a pulse control unit 211 may cause a gradient signal generation unit 212 to generate gradient signals along different directions (e.g., the X direction, the Y direction, and/or the Z direction). The gradient signals may be amplified by the X gradient amplifier 213, the Y gradient amplifier 214, and/or the Z gradient amplifier 215. The amplified gradient signals may be emitted by the gradient coils 202, and the gradient fields (e.g., Gx, Gy, and/or Gz) may be generated in the region 205. In some instances, all three sets of coils of the gradient coils 202 may be energized and three gradient fields may be generated thereby. In some embodiments of the present disclosure, the X coils and Y coils may be energized to generate the gradient fields in the X direction and the Y direction. As used herein, the X-axis, the Y-axis, the Z-axis, the X direction, the Y direction, and the Z direction in the description of FIG. 2 are the same as or similar to those described in FIG. 1.

In some embodiments, radio frequency (RF) coils may be located inside the main magnet 201 and serve as transmitters, receivers, or both. The RF coils may be in connection with RF electronics that may be configured or used as one or more integrated circuits (ICs) functioning as a waveform transmitter and/or waveform receiver. The RF electronics may be connected to a radiofrequency power amplifier (RFPA) and an analog-to-digital converter (ADC).

In some embodiments, the RF coils may include one or more RF transmit coils and/or one or more RF receiver coils. The RF transmit coil(s) may transmit RF pulses to the patient 250. Under the coordinated action of the main magnetic field, the gradient magnetic field, and the RF pulses, MR signals relating to the subject may be generated according to a pulse sequence. The RF receiver coils may acquire MR signals from the subject according to the pulse sequence. In some embodiments, an RF receiver coil may correspond to a channel for acquiring MR signals. The RF receiver coils may receive a plurality of channels of MRI signals from the subject.

When used as transmitters, the RF coils may generate RF signals that provide a third magnetic field that is utilized to generate echo signals related to the region of the object being imaged. The third magnetic field may be perpendicular to the main magnetic field. The waveform generator may generate an RF pulse. The RF pulse may be amplified by the RFPA, processed by the RF electronics, and applied to the RF coils to generate the RF signals in response to a powerful current generated by the RF electronics based on the amplified RF pulse.

When used as receivers, the RF coils may be responsible for detecting echo signals. After excitation, the echo signals generated by the subject may be sensed by the RF coils. The receive amplifier then may receive the sensed echo signals from the RF coils, amplify the sensed echo signals, and provide the amplified echo signals to the ADC. The ADC may transform the echo signals from analog signals to digital signals. The digital echo signals then may be sent to the processing device 120 for sampling.

In some embodiments, the RF coils may include a body coil 203 and a local coil 204. In some embodiments, during the MRI scan, the pulse control unit 211 may cause an RF pulse generation unit 216 to generate RF pulses. After the RF pulses are amplified by an amplifier, the RF pulses may be emitted by the RF coils (e.g., the body coil 203, the local coil 204) by controlling a switch control unit 217, and an RF excitation may be performed on the patient 250. RF signals may be generated based on the RF excitation on the patient 250. The RF signals may be received by the RF coils (e.g., the body coil 203, the local coil 204), and then transmitted to an RF receiving unit 218 and an image reconstruction unit 221 for image reconstruction.

In some embodiments, the gradient coils 202 and the RF coils may be circumferentially positioned with respect to the patient 250. It is understood by those skilled in the art that the main magnet 201, the gradient coils 202, and the RF coils may be situated in a variety of configurations around the patient 250.

In some embodiments, the RFPA may amplify an RF pulse (e.g., the power of the RF pulse, the voltage of the RF pulse) such that an amplified RF pulse is generated to drive the RF coils. The RFPA may include a transistor-based RFPA, a vacuum tube-based RFPA, or the like, or any combination thereof. The transistor-based RFPA may include one or more transistors. The vacuum tube-based RFPA may include a triode, a tetrode, a klystron, or the like, or any combination thereof. In some embodiments, the RFPA may include a linear RFPA, or a nonlinear RFPA. In some embodiments, the RFPA may include one or more RFPAs.

MRI systems (e.g., the medical system 100 or the medical system 200 disclosed in the present disclosure) may be commonly used to obtain an interior image from a patient for a particular region of interest (ROI) that can be used for the purposes of, e.g., diagnosis, treatment, or the like, or a combination thereof. MRI systems include a main magnet (e.g., the main magnet 201) assembly for providing a strong uniform main magnetic field to align the individual magnetic moments of the H atoms within the patient's body. During this process, the H atoms oscillate around their magnetic poles at their characteristic Larmor frequency. If the tissue is subjected to an additional magnetic field, which is tuned to the Larmor frequency, the H atoms absorb additional energy, which rotates the net aligned moment of the H atoms. The additional magnetic field may be provided by an RF excitation signal (e.g., the RF signal generated by the RF coils). When the additional magnetic field is removed, the magnetic moments of the H atoms rotate back into alignment with the main magnetic field thereby emitting an echo signal. The echo signal is received and processed to form an MRI image. If the main magnetic field is uniform across the entire body of the patient, then the RF excitation signal may excite all of the H atoms in the sample non-selectively. Accordingly, in order to image a particular portion of the patient's body, magnetic field gradients Gx, Gy, and Gz (e.g., generated by the gradient coils 202) in the X, Y, and Z directions, having a particular timing, frequency, and phase, may be superimposed on the uniform magnetic field such that the RF excitation signal excites the H atoms in a desired slice of the patient's body, and unique phase and frequency information is encoded in the echo signal depending on the location of the H atoms in the "image slice."

The computing device may include a processor 222, a display unit 223, an input/output device 224, and a storage device 225, A method for determining target position information of the target subject may be stored in the storage device 225 as a form of instructions, and invoked and/or executed by the processor 222. The processor 222 may be configured to execute the method for determining target position information of the target subject as described elsewhere the present disclosure.

The processor 222 may include one or more processors, such as a microcontroller, a microprocessor, a reduced instruction set computer (RISC), an application specific integrated circuit (ASIC), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

The display unit 223 may be configured to display an image for a user (e.g., a doctor, a technician, an operator). For example, the display unit 223 may display an image reflecting position information of a target subject for a doctor.

The input/output device 224 may input and/or output signals, data, information, etc. In some embodiments, the input/output device 224 may enable a user interaction with the computing device. In some embodiments, the input/output device 224 may include an input device and an output device. Examples of the input device may include a keyboard, a mouse, a touch screen, a microphone, or the like, or any combination thereof. Examples of the output device may include a display device, a loudspeaker, a printer, a projector, or the like, or any combination thereof. Examples of the display device may include a liquid crystal display (LCD), a light-emitting diode (LED)-based display, a flat panel display, a curved screen, a television device, a cathode ray tube (CRT), a touch screen, or the like, or any combination thereof.

The storage device 225 may store data, instructions, and/or any other information. The storage device 225 may include a hard disk drive (HDD), a soft disk drive, a flash drive, a photomagnetic disk, an optical disk, a magnetic tape, a universal serial bus (USB) drive, or the like, or any combinations thereof. In some embodiments, the storage device 225 may include a removable or non-removable medium. In some embodiments, the storage device 225 may include a non-volatile solid-state memory. In some embodiments, the storage device 225 may include a read-only memory (ROM). The ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, an electrically alterable ROM (EAROM), or the like, or any combinations thereof. In some embodiments, the storage device 225 may include a random-access memory (RAM). The RAM may include a static RAM (SRAM), a dynamic RAM (DRAM), etc. The DRAM may include a fast page mode dynamic RAM (FPMDRAM), an extended date out dynamic RAM (EDODRAM), a synchronous dynamic RAM (SDRAM), etc. In some embodiments, the storage device 225 may store data to be processed and/or communicated and one or more programs and/or instructions to perform exemplary methods described in the present disclosure. When the one or more programs and/or instructions stored in the storage device 225 are performed, the processor 222 may perform the mothed for determining the target position information of the target subject as described in the present disclosure. The storage device 225 may be similar to the storage device 130. In some embodiments, the storage device 225 and the processor 222 may be combined into a single device. In some embodiments, the storage device 225 and the processor 222 may be two devices.

The communication port 226 may connected to a network to facilitate data communications. The communication port 226 may establish connections between the computing device (e.g., the processor 222, the display unit 223, the input/output device 224, the storage device 225) and one or more components of the medical system 200 (e.g., an external device, an image acquisition device, a database, an external storage, an image processing workstation).

The communication bus 227 may include hardware, software, or a combination thereof. The communication bus 227 may establish connections between components of the medical system 200. For example, the communication bus 227 may include a graphics bus (e.g., an accelerated graphics port (AGP)), an enhanced industry standard architecture (EISA) bus, a front side bus (FSB), a hypertransport (HT) interconnection, an industry standard architecture (ISA) bus, an infinite bandwidth interconnect, a low pin count (LPC) bus, a memory bus, a micro channel architecture (MCA) bus, a peripheral component interconnect (PCI) bus, a PCI-express (PCI-X) bus, a serial advanced technology attachment (SATA) bus, a video electronics standards association local (VLB) bus, or the like, or any combinations thereof. In some embodiments, the communication bus 227 may include one or more buses.

In some embodiments, the pulse control unit 211, the image reconstruction unit 221, the processor 222, the display unit 223, the input/output device 224, the storage device 225, and the communication port 226 may transmit data through the communication bus 227 to control the MRI scan of the patient 250.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure.

Figure 3:
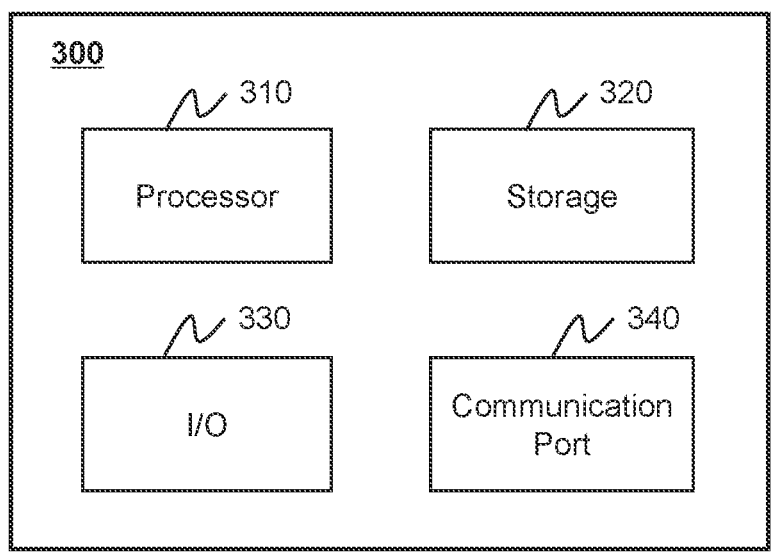
FIG. 3 is a schematic diagram illustrating exemplary hardware and/or software components of an exemplary computing device according to some embodiments of the present disclosure

FIG. 3 is a schematic diagram illustrating exemplary hardware and/or software components of an exemplary computing device according to some embodiments of the present disclosure. In some embodiments, one or more components of the medical system 100 may be implemented on one or more components of the computing device 300. Merely by way of example, the processing device 120 and/or the terminal(s) 140 may be implemented one or more components of the computing device 300, respectively.

As illustrated in FIG. 3, the computing device 300 may include a processor 310, a storage device 320, an input/output (I/O) 330, and a communication port 340. The processor 310 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 310 may process image data of a subject obtained from the medical device 110, the storage device 130, terminal(s) 140, and/or any other component of the medical system 100.

In some embodiments, the processor 310 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof.

Merely for illustration, only one processor is described in the computing device 300. However, it should be noted that the computing device 300 in the present disclosure may also include multiple processors. Thus operations and/or method steps that are performed by one processor as described in the present disclosure may also be jointly or separately performed by the multiple processors. For example, if in the present disclosure the processor of the computing device 300 executes both operation A and operation B, it should be understood that operation A and operation B may also be performed by two or more different processors jointly or separately in the computing device 300 (e.g., a first processor executes operation A and a second processor executes operation B, or the first and second processors jointly execute operations A and B).

The storage device 320 may store data/information obtained from the medical device 110, the storage device 130, the terminal(s) 140, and/or any other component of the medical system 100. In some embodiments, the storage device 320 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random-access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 320 may store one or more programs and/or instructions to perform exemplary methods described in the present disclosure.

The I/O 330 may input and/or output signals, data, information, etc. In some embodiments, the I/O 330 may enable a user interaction with the computing device 300 (e.g., the processing device 120). In some embodiments, the I/O 330 may include an input device and an output device. Examples of the input device may include a keyboard, a mouse, a touch screen, a microphone, or the like, or any combination thereof. Examples of the output device may include a display device, a loudspeaker, a printer, a projector, or the like, or any combination thereof. Examples of the display device may include a liquid crystal display (LCD), a light-emitting diode (LED)-based display, a flat panel display, a curved screen, a television device, a cathode ray tube (CRT), a touch screen, or the like, or any combination thereof.

The communication port 340 may be connected to a network (e.g., the network 150) to facilitate data communications. The communication port 340 may establish connections between the computing device 300 (e.g., the processing device 120) and one or more components of the medical system 100 (e.g., the medical device 110, the storage device 130, and/or the terminal(s) 140). The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or any combination thereof. In some embodiments, the communication port 340 may be and/or include a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
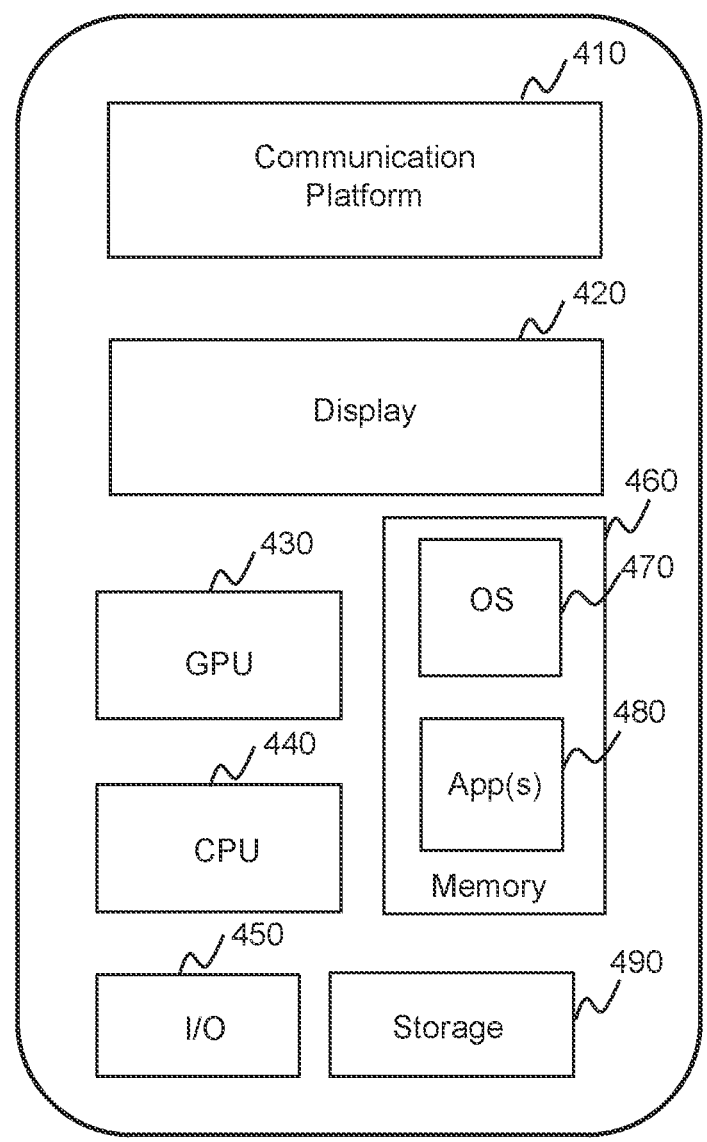
FIG. 4 is a schematic diagram illustrating exemplary hardware and/or software components of an exemplary mobile device on which a terminal device may be implemented according to some embodiments of the present disclosure.

FIG. 4 is a schematic diagram illustrating exemplary hardware and/or software components of an exemplary mobile device on which a terminal device may be implemented according to some embodiments of the present disclosure. In some embodiments, one or more components of the medical system 100 may be implemented on one or more components of the mobile device 400. Merely by way of example, the terminal 140 may be implemented on one or more components of the mobile device 400.

As illustrated in FIG. 4, the mobile device 400 may include a communication platform 410, a display 420, a graphics processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS™, Android™, Windows Phone™, etc.) and one or more applications 480 may be loaded into the memory 460 from the storage 490 in order to be executed by the CPU 440. The applications 480 may include a browser or any other suitable mobile apps for receiving and rendering information relating to the medical system 100. User interactions with the information stream may be achieved via the I/O 450 and provided to the processing device 120 and/or other components of the medical system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal. A computer may also act as a server if appropriately programmed.

Figure 5:
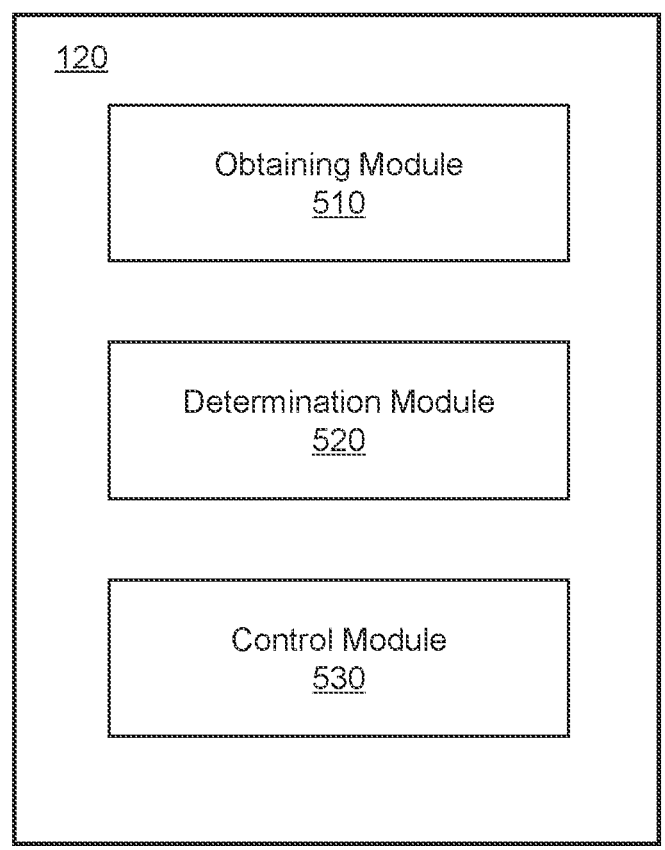
FIG. 5 is a schematic diagram illustrating an exemplary processing device according to some embodiments of the present disclosure.

FIG. 5 is a schematic diagram illustrating an exemplary processing device according to some embodiments of the present disclosure. In some embodiments, the processing device 120 may include an obtaining module 510, a determination module 520, and a control module 530. In some embodiments, the modules may be hardware circuits of all or part of the processing device 120. The modules may also be implemented as an application or set of instructions read and executed by the processing device 120. Further, the modules may be any combination of the hardware circuits and the application/instructions. For example, the modules may be part of the processing device 120 when the processing device 120 is executing the application/set of instructions.

The obtaining module 510 may be configured to obtain data and/or information associated with the medical system 100. The data and/or information associated with the medical system 100 may include target magnetic field information of a target subject (e.g., a scan region of a patient, an operating element), information of at least one pair of magnetic resonance peaks of a diamond NV center in a diamond NV center sensor, magnetic field distribution information of a reference magnetic field, a medical image (e.g., an MRI image), position information of a subject (e.g., a target subject, a reference subject, a candidate subject), relative position information between two subjects, or the like, or any combination thereof. For example, the obtaining module 510 may obtain, via a plurality of sensors (e.g., a plurality of diamond NV center sensors), real-time target magnetic field information of a target subject. As another example, the obtaining module 510 may obtain reference position information of a reference subject in a medical system (e.g., the medical system 100). As another example, the obtaining module 510 may obtain first relative position information between a candidate subject and a reference subject. In some embodiments, the obtaining module 510 may obtain the data and/or the information associated with the medical system 100 from one or more components (e.g., the medical device 110, the storage device 130, the terminal 140) of the medical system 100 via the network 150.

The determination module 520 may be configured to determine data and/or information associated with the medical system 100. In some embodiments, the determination module 520 may determine real-time target position information of a target subject based on real-time target magnetic field information of the target subject and magnetic field distribution information of a reference magnetic field in a medical system. For example, for each pair of at least one pair of magnetic resonance peaks of a diamond NV center, the determination module 520 may determine candidate magnetic field information related to a corresponding crystal axis direction of the diamond NV center based on information of the pair of magnetic resonance peaks. The determination module 520 may determine real-time target magnetic field information based on the candidate magnetic field information of the diamond NV center and a coordinate transformation relationship between a crystal coordinate system of the diamond NV center and a magnetic field coordinate system of the reference magnetic field. More descriptions for determining the target position information of the target subject may be found elsewhere in the present disclosure (e.g., FIGS. 6-7 and descriptions thereof). In some embodiments, the determination module 520 may determine second relative position information between a target subject (e.g., an operating element) and a reference subject based on target position information of the target subject and reference position information of the reference subject. In some embodiments, the determination module 520 may determine third relative position information between a target subject (e.g., an operating element) and a candidate subject (e.g., a patient) based on first relative position information and second relative position information. More descriptions for determining the second relative position information and the third relative position information may be found elsewhere in the present disclosure (e.g., FIG. 8 and descriptions thereof).

The control module 530 may be configured to control a component (e.g., the medical device 110) of the medical system 100. For example, the control module 530 may cause a medical device (e.g., the medical device 110) to scan a target subject (e.g., a scan region of a patient) based on motion information of the target subject. As another example, the control module 530 may cause a terminal device (e.g., the terminal 140) to display an image reflecting third relative position information between a target subject (e.g., an operating element) and a candidate subject (e.g., a patient).

It should be noted that the above description of the processing device 120 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more modules may be combined into a single module. For example, the obtaining module 510 and the determination module 520 may be combined into a single module. In some embodiments, one or more modules may be added or omitted in the processing device 120. For example, the control module 530 may be omitted. As another example, a storage module (not shown in FIG. 5) may be added in the processing device 120. The storage module may be configured to store information (e.g., information of at least one pair of magnetic resonance peaks of a diamond NV center in at least one diamond NV center sensor, target magnetic field information of a target subject, target position information of a target subject) associated with the medical system 100.

Figure 6:
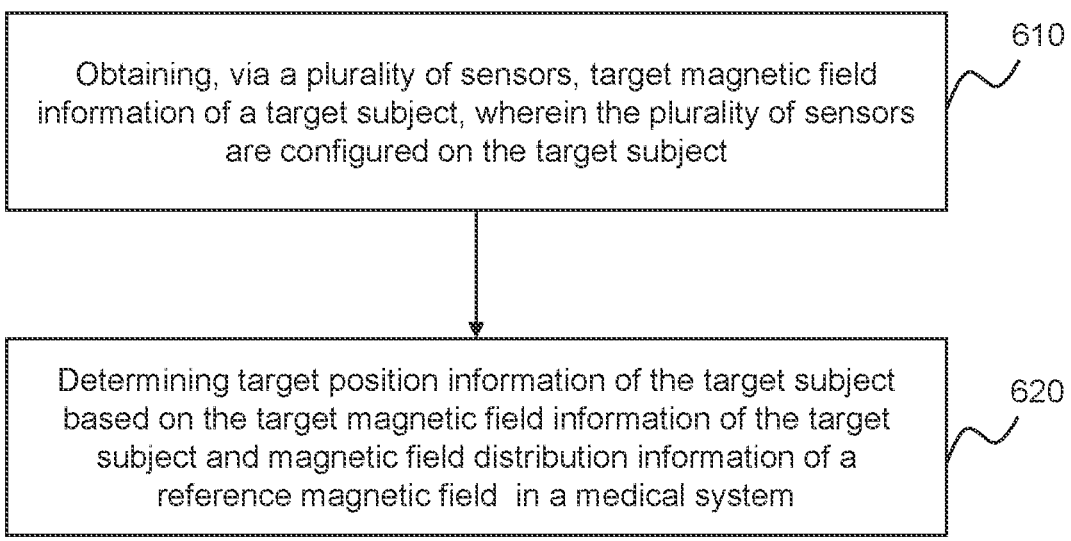
FIG. 6 is a flowchart illustrating an exemplary process for determining target position information of a target subject according to some embodiments of the present disclosure.

FIG. 6 is a flowchart illustrating an exemplary process for determining target position information of a target subject according to some embodiments of the present disclosure. In some embodiments, process 600 may be implemented in the medical system 100 or the medical system 200 illustrated in FIG. 1. For example, the process 600 may be stored in the storage device 130 and/or the storage (e.g., the storage device 320, the storage 490) as a form of instructions, and invoked and/or executed by the processing device 120 (e.g., the processor 222 as illustrated in FIG. 2, the processor 310 of the computing device 300 as illustrated in FIG. 3, the CPU 440 of the mobile device 400 as illustrated in FIG. 4). The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In 610, the processing device 120 (e.g., the obtaining module 510) may obtain, via a plurality of sensors (e.g., a plurality of diamond NV center sensors), target magnetic field information of a target subject. The plurality of sensors may be configured on the target subject. The target subject may be located in a reference magnetic field in a medical system.

In some embodiments, the sensor may include a diamond NV center sensor. In some embodiments, the diamond NV center sensor may be mounted on any suitable position of the target subject, as described elsewhere in the present disclosure (e.g., FIG. 2, and descriptions thereof). The target subject may include a scan region of a patient, an operating element, or the like. For example, the target subject may be the scan region of the patient. The target magnetic field information of the scan region corresponding to different time points may be used for determining the motion information of the scan region. A medical device may be caused to scan the scan region based on the motion information of the scan region. More descriptions for determining the motion information of the scan region may be found elsewhere in the present disclosure (e.g., FIG. 7 and descriptions thereof). As another example, the target subject may be the operating element. The target magnetic field information of the operating element may be used for determining the position information of the operating element. The position of the operating element may be displayed to a user (e.g., a doctor) of the medical system 100 in (substantially) real time for monitoring and/or guiding a medical operation. More descriptions for displaying the position information of the operating element may be found elsewhere in the present disclosure (e.g., FIG. 8 and descriptions thereof).

As used herein, target magnetic field information refers to a magnetic field strength vector corresponding to a magnetic field direction in a magnetic field coordinate system of a reference magnetic field. In some embodiments, different magnetic field coordinate systems may be constructed for different reference magnetic fields. For example, the magnetic field coordinate system may be similar to the coordinate system 160 including the X-axis, the Y-axis, and the Z-axis, as illustrated in FIGS. 1-2. In some embodiments, the reference magnetic field may include one or more magnetic fields. In some embodiments, the reference magnetic field may include a plurality of magnetic fields along different directions. For example, the reference magnetic field may include a first magnetic field along a first magnetic field direction (e.g., the X-axis direction of the coordinate system 160 as illustrated in FIG. 1), a second magnetic field along a second magnetic field direction (e.g., the Y-axis direction of the coordinate system 160 as illustrated in FIG. 1), and a third magnetic field along a third magnetic field direction (e.g., the Z-axis direction of the coordinate system 160 as illustrated in FIG. 1).

In some embodiments, in an MRI system, the reference magnetic field may include a main magnetic field, a gradient field (e.g., gradient fields Gx, Gy, and Gz), or the like, as described elsewhere in the present disclosure (e.g., FIG. 2, and descriptions thereof). The target magnetic field information may include main magnetic field information, gradient field information, or the like, or any combination thereof. The main magnetic field may be generated by a main magnet (e.g., the main magnet 201) of the MRI device. The gradient field may be generated by a gradient coil (e.g., the gradient coils 202) of the MRI device. For example, the reference magnetic field may include the main magnetic field. The target magnetic field information of the target subject (e.g., the patient) located in the main magnetic field may be used for determining physiological motion information (e.g., cardiac motion information, respiratory motion information) of the target subject (e.g., the patient). As another example, the reference magnetic field may include the main magnetic field and a plurality of gradient fields (e.g., gradient fields Gx, Gy, and Gz). The target magnetic field information of the target subject (e.g., the patient) located in the main magnetic field and the plurality of gradient fields may be used for determining posture information of the target subject (e.g., the patient). More descriptions for determining the motion information of the patient may be found elsewhere in the present disclosure (e.g., FIG. 7 and descriptions thereof).

In some embodiments, in a medical system (e.g., a PET system, a SPECT system, a CT system, an RT system) that does not employ a magnetic field for imaging and/or treatment, an external magnetic field generating device may be used to generate the reference magnetic field.

In some embodiments, the processing device 120 may obtain, via the plurality of diamond NV center sensors, the target magnetic field information of the target subject. In some embodiments, the processing device 120 may obtain information of at least one pair of magnetic resonance peaks of a diamond NV center in the diamond NV center sensor.

The at least one pair of magnetic resonance peaks of the diamond NV center may be obtained by splitting a total magnetic resonance peak of the diamond NV center via the reference magnetic field. The total magnetic resonance peak of the diamond NV center refers to a single resonance peak (e.g., at 2.87 GHz) in a fluorescence spectrum of the diamond NV center when no external magnetic field is applied on the diamond NV center. When an external magnetic field (e.g., the reference magnetic field) is applied on the diamond NV center, the total magnetic resonance peak of the diamond NV center may be splitted into at least one pair of magnetic resonance peaks. Each pair of the at least one pair of magnetic resonance peaks may correspond to a crystal axis direction of the diamond NV center. The crystal axis may be parallel to an edge of a unit cell of a crystal structure and parallel to a symmetry direction of the crystal structure. For example, for a diamond NV center having a diamond cubic lattice structure, the diamond NV center may include (111) crystal axis, (1-11) crystal axis, (-111) crystal axis, and (11-1) crystal axis of the diamond cubic lattice structure.

In some embodiments, the total magnetic resonance peak of the diamond NV center may be splitted into a first pair of magnetic resonance peaks, a second pair of magnetic resonance peaks, a third pair of magnetic resonance peaks, and a fourth pair of magnetic resonance peaks, via the reference magnetic field. Each pair of magnetic resonance peaks of the diamond NV center may correspond to one crystal axis direction (e.g., the crystal axis direction (111), the crystal axis direction (1-11), the crystal axis direction (-111), the crystal axis direction (11-1)) of the diamond NV center.

Figure 10:
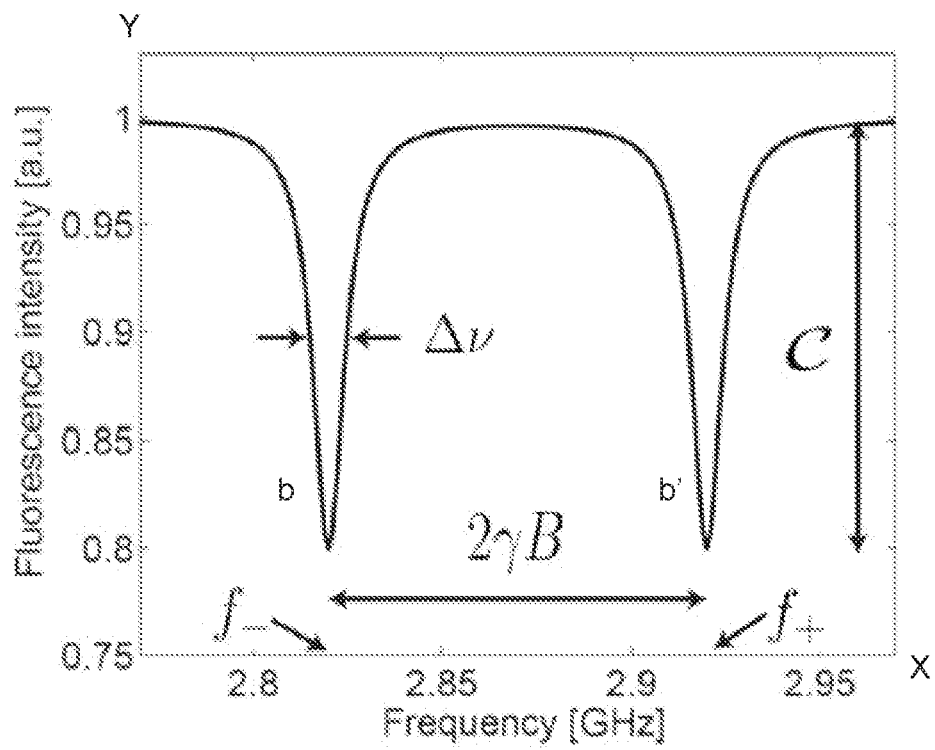
FIG. 10 is an enlarged view of a pair of magnetic resonance peaks of the diamond NV center in the ODMR spectrum shown in FIG. 9 according to some embodiments of the present disclosure.

In some embodiments, the processing device 120 may obtain the information of the at least one pair of magnetic resonance peaks of the diamond NV center in the diamond NV center sensor based on an optically detected magnetic resonance (ODMR) spectrum of the diamond NV center. The ODMR spectrum may be obtained by recording a fluorescence intensity of the diamond NV center as a function of an applied microwave frequency. The information of at least one pair of magnetic resonance peaks may include a probe microwave frequency of each magnetic resonance peak, a fluorescence intensity of each magnetic resonance peak (e.g., a fluorescence intensity C as illustrated in FIG. 10), a linewidth (e.g., a full width at half-maximum (FWHM)) of each magnetic resonance peak (e.g., a linewidth $\Delta v$ as illustrated in FIG. 10), or the like, or any combination thereof. In some embodiments, the fluorescence intensity of the magnetic resonance peak and the linewidth of the magnetic resonance peak may be used to characterize the peak discrimination in the ODMR spectrum. For example, if the fluorescence intensity of a specific magnetic resonance peak and/or the linewidth of the specific magnetic resonance peak is relatively small (e.g., smaller than a threshold), it may be difficult to identify the specific magnetic resonance peak in the ODMR spectrum.

Figure 9:
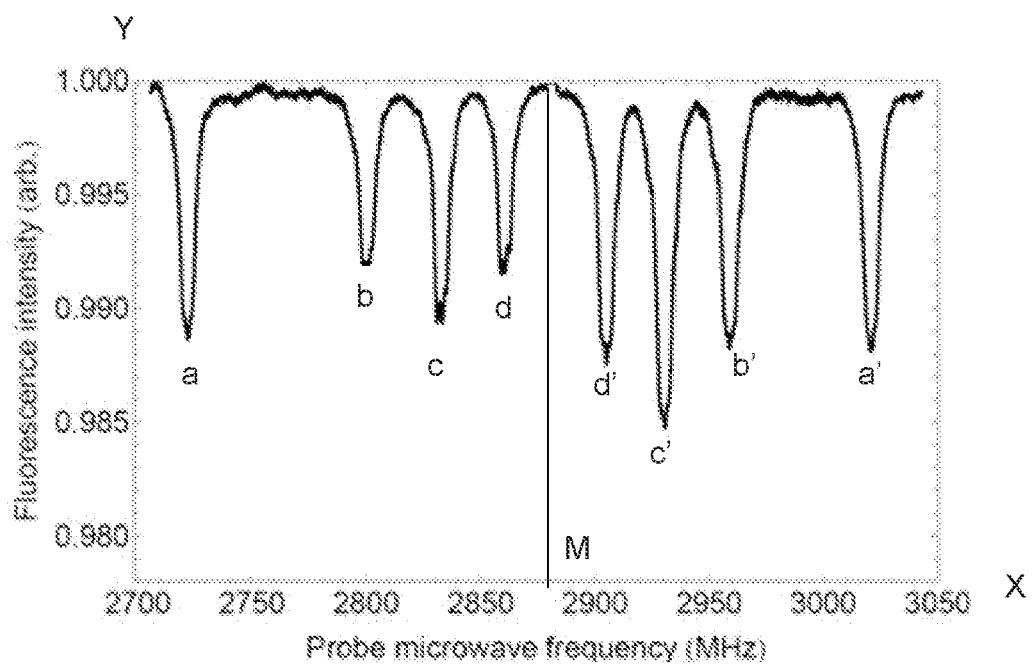
FIG. 9 is a schematic diagram illustrating an exemplary optically detected magnetic resonance (ODMR) spectrum of a diamond NV center according to some embodiments of the present disclosure.

FIG. 9 is a schematic diagram illustrating an exemplary ODMR spectrum of a diamond NV center according to some embodiments of the present disclosure. FIG. 10 is an enlarged view of a pair of magnetic resonance peaks of the diamond NV center in the ODMR spectrum shown in FIG. 9 according to some embodiments of the present disclosure. As illustrated in FIGS. 9 and 10, the X-axis indicates a probe microwave frequency, and the Y-axis indicates a fluorescence intensity. Under the action of the reference magnetic field, the total magnetic resonance peak of the diamond NV center may be splitted into a first pair of magnetic resonance peaks (e.g., magnetic resonance peaks a and a'), a second pair of magnetic resonance peaks (e.g., magnetic resonance peaks b and b'), a third pair of magnetic resonance peaks (e.g., magnetic resonance peaks c and c'), and a fourth pair of magnetic resonance peaks (e.g., magnetic resonance peaks d and d'). The two magnetic resonance peaks in each pair of magnetic resonance peaks may be symmetrically distributed along the X-axis with the probe microwave frequency at a point M as the center. For instance, the X-axis coordinate of the point M may be 2.87 GHz as illustrated. Each pair of magnetic resonance peaks of the diamond NV center may correspond to one crystal axis direction of the diamond NV center. For example, the first pair of magnetic resonance peaks may correspond to the crystal axis direction (111) of the diamond NV center; the second pair of magnetic resonance peaks may correspond to the crystal axis direction (1–11) of the diamond NV center; the third pair of magnetic resonance peaks may correspond to the crystal axis direction (–111) of the diamond NV center; the fourth pair of magnetic resonance peaks may correspond to the crystal axis direction (11–1) of the diamond NV center.

Further, the processing device 120 may obtain the target magnetic field information of the target subject based on the information of the at least one pair of magnetic resonance peaks of the diamond NV center. In some embodiments, for each pair of the at least one pair of magnetic resonance peaks of the diamond NV center, the processing device 120 may determine candidate magnetic field information related to the corresponding crystal axis direction of the diamond NV center based on the information of the pair of magnetic resonance peaks. As used herein, candidate magnetic field information refers to a magnetic field strength vector corresponding to a crystal axis direction in a crystal coordinate system of a diamond NV center. In some embodiments, different crystal coordinate systems may be constructed for crystals of different structures. Merely by way of example, for the crystal coordinate system of the diamond NV center, an origin may be a center point of the diamond NV center, and the crystal axis (1–11), the crystal axis (–111), and the crystal axis (111) of the diamond NV center may be determined as the coordinate axes of the crystal coordinate system.

For example, for each pair of the at least one pair of magnetic resonance peaks of the diamond NV center, the processing device 120 may determine the candidate magnetic field information related to the corresponding crystal axis direction of the diamond NV center based on a relationship between the information of the pair of magnetic resonance peaks (e.g., a difference between probe microwave frequencies of two magnetic resonance peaks in the pair of magnetic resonance peaks) and the candidate magnetic field information. In some embodiments, the relationship may be determined based on structural properties of the diamond NV center. For example, the relationship between the difference between probe microwave frequencies of the two magnetic resonance peaks in the pair of magnetic resonance peaks, and the candidate magnetic field information may be represented according to Equation (1):

$$f_\pm = f_+ - f_- = 2\gamma B, \quad (1)$$

where $f_+$ refers to a probe microwave frequency of a first magnetic resonance peak (e.g., a magnetic resonance peak b' as illustrated in FIG. 10) of a pair of magnetic resonance peaks; $f_-$ refers to a probe microwave frequency of a second magnetic resonance peak (e.g., a magnetic resonance peak b as illustrated in FIG. 10) of the pair of magnetic resonance peaks; $f_\pm$ refers to a splitting width of the two magnetic resonance peaks in the pair of magnetic resonance peaks (i.e., a difference between a first probe microwave frequency of the first magnetic resonance peak and a second probe microwave frequency of the second magnetic resonance peak); $\gamma$ refers to a gyromagnetic ratio of the diamond NV center; B refers to candidate magnetic field information related to a corresponding crystal axis direction of the diamond NV center.

The processing device 120 may determine the target magnetic field information based on the candidate magnetic field information of the diamond NV center and a coordinate transformation relationship between the crystal coordinate system of the diamond NV center and the magnetic field coordinate system of the reference magnetic field. The coordinate transformation relationship may represent a position relationship between the crystal coordinate system and the magnetic field coordinate system. The position relationship between the crystal coordinate system and the magnetic field coordinate system may include an included angle between each crystal axis of the crystal coordinate system and each magnetic field direction of the magnetic field coordinate system. In some embodiments, the coordinate transformation relationship may be determined by one or more components (e.g., the processing device 120) of the medical system 100, or a user of the medical system 100, and stored in a storage device of the medical system 100. The processing device 120 may access the storage device and retrieve the coordinate transformation relationship when determining the target magnetic field information.

In some embodiments, the processing device 120 may determine the target magnetic field information based on the candidate magnetic field information related to different crystal axis directions of the diamond NV center. In some embodiments, the processing device 120 may determine a magnetic field strength vector corresponding to a magnetic field direction in the magnetic field coordinate system based on the coordinate transformation relationship, and a magnetic field strength vector corresponding to the crystal axis direction. For example, the processing device 120 may determine the magnetic field strength vector corresponding to the magnetic field direction in the magnetic field coordinate system based on the magnetic field strength vector corresponding to the crystal axis direction, and an included angle between the crystal axis direction and the magnetic field direction.

In some embodiments, the diamond NV center sensor may determine the target magnetic field information based on the information of at least one pair of magnetic resonance peaks of the diamond NV center directly. The processing device 120 may obtain the target magnetic field information determined by the diamond NV center sensor, and determine the target position information of the target subject based on the target magnetic field information of the target subject. In some embodiments, the processing device 120 may obtain the information of at least one pair of magnetic resonance peaks of the diamond NV center from the diamond NV center sensor, and determine the target magnetic field information based on the information of at least one pair of magnetic resonance peaks of the diamond NV center. In some embodiments, the target magnetic field information of the target subject may be obtained from the plurality of sensors in real time, and the target position information of the target subject may be determined based on the target magnetic field information of the target subject in real time. That is, real-time target magnetic field information of the target subject may be obtained, and real-time target position information of the target subject may be determined based on the real-time target magnetic field information of the target subject.

In some embodiments, the processing device 120 may obtain the information of at least one pair of magnetic resonance peaks of the diamond NV center and/or the target magnetic field information from the diamond NV center sensor directly. In some embodiments, the at least one diamond NV center sensor may transmit the information of at least one pair of magnetic resonance peaks of the diamond NV center and/or the target magnetic field information to a storage device (e.g., the storage device 130). Further, the processing device 120 may access the storage device 130 and retrieve the information of at least one pair of magnetic resonance peaks of the diamond NV center and/or the target magnetic field information.

In 620, the processing device 120 (e.g., the determination module 520) may determine target position information of the target subject based on the target magnetic field information of the target subject and magnetic field distribution information of the reference magnetic field in the medical system.

In some embodiments, the target position information may include coordinates (e.g., X-axis coordinates, Y-axis coordinates, Z-axis coordinates) of the target subject in the magnetic field coordinate system of the reference magnetic field. In some embodiments, the target position information may include a center position of the X-axis in a slice (also referred to as an anatomical slice as described in FIGS. 1 and 2), a center position of the Y axis in the slice, a center position of the Z-axis in the slice, a normal vector of the X-axis, a normal vector of the Y-axis, a normal vector of the Z-axis, and a rotation angle of the slice.

The magnetic field distribution information of the reference magnetic field may reflect a relationship between target position information of the target subject in the reference magnetic field and target magnetic field information of the target subject in the reference magnetic field. That is, each spatial position in the reference magnetic field may correspond to specific magnetic field information (e.g., one or more specific magnetic field strength vectors each corresponding to a magnetic field direction of the reference magnetic field). For example, an MRI device may include gradient coils (e.g., gradient coils 202) configured to generate different magnetic fields (e.g., gradient fields Gx, Gy, and Gz) that are used for position encoding, as described elsewhere in the present disclosure (e.g., FIG. 2 and descriptions thereof). The magnetic field distribution information of the reference magnetic field may be determined based on parameters of the MRI device. The parameters of the MRI device may include positions of the gradient coils (e.g., X coils, Y coils, Z coils), directions of gradient fields (e.g., the gradient fields Gx, Gy, Gz), strengths of gradient fields (e.g., the gradient fields Gx, Gy, Gz), or the like, or any combination thereof.

The processing device 120 may determine the target position information of the target subject based on the target magnetic field information of the target subject, and the relationship between target position information of the target subject in the reference magnetic field and target magnetic field information of the target subject in the reference magnetic field.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more other optional operations may be added in process 600. For example, an operation for storing information (e.g., the information of the at least one pair of magnetic resonance peaks of the diamond NV center in the at least one diamond NV center sensor, the target magnetic field information of the target subject, the target position information of the target subject) associated with the medical system 100 may be added in process 600. As another example, an operation for displaying the target position information of the target subject (e.g., an operating element) may be added in process 600. As still another example, an operation for determining motion information of the target subject (e.g., a scan region of a patient) between different time points may be added in process 600.

Figure 7:
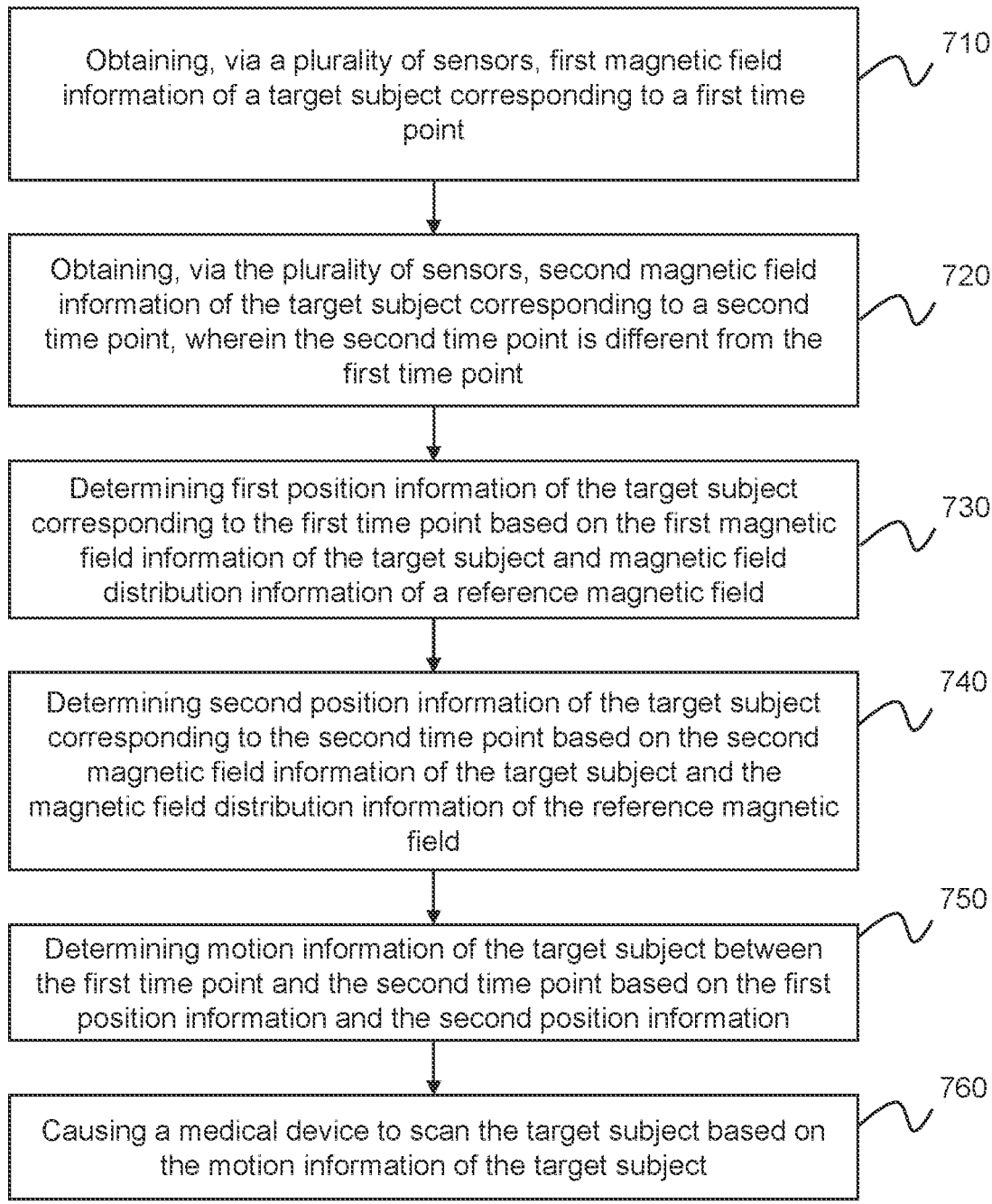
FIG. 7 is a flowchart illustrating an exemplary process for determining motion information of a target subject according to some embodiments of the present disclosure.

FIG. 7 is a flowchart illustrating an exemplary process for determining motion information of a target subject according to some embodiments of the present disclosure. In some embodiments, process 600 may be implemented in the medical system 100 or the medical system 200 illustrated in FIG. 1. For example, the process 700 may be stored in the storage device 130 and/or the storage (e.g., the storage device 320, the storage 490) as a form of instructions, and invoked and/or executed by the processing device 120 (e.g., the processor 222 as illustrated in FIG. 2, the processor 310 of the computing device 300 as illustrated in FIG. 3, the CPU 440 of the mobile device 400 as illustrated in FIG. 4). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In 710, the processing device 120 (e.g., the obtaining module 510) may obtain, via a plurality of sensors (e.g., a plurality of diamond NV center sensors), first magnetic field information of a target subject corresponding to a first time point.

In some embodiments, the target subject may be a scan region of a patient to be scanned by a medical device (e.g., the medical device 110). In some embodiments, the NV center sensor may be configured to obtain magnetic field information of the scan region of the patient continuously or intermittently (e.g., periodically) before, during, and/or after a scan of the scan region performed by the medical device 110. In some embodiments, the first time point may be any time point or any time period during the scan of the scan region. The first magnetic field information may be determined in a similar manner as that of the target magnetic field information as described elsewhere in the present disclosure (e.g., operation 610 in FIG. 6 and descriptions thereof).

In 720, the processing device 120 (e.g., the obtaining module 510) may obtain, via the plurality of sensors (e.g., the plurality of diamond NV center sensors), second magnetic field information of the target subject corresponding to a second time point.

The second time point may be different from the first time point. For example, the second time point may be a time point or a time period before or after the first time point during the scan of the scan region of the patient. The second magnetic field information may be determined in a similar manner as that of the target magnetic field information as described elsewhere in the present disclosure (e.g., operation 610 in FIG. 6 and descriptions thereof).

In 730, the processing device 120 (e.g., the determination module 520) may determine first position information of the target subject corresponding to the first time point based on the first magnetic field information of the target subject and magnetic field distribution information of a reference magnetic field.

The first position information may be determined in a similar manner as that of the target position information as described elsewhere in the present disclosure (e.g., operation 620 in FIG. 6 and descriptions thereof).

In 740, the processing device 120 (e.g., the determination module 520) may determine second position information of the target subject corresponding to the second time point based on the second magnetic field information of the target subject and the magnetic field distribution information of the reference magnetic field.

The second position information may be determined in a similar manner as that of the target position information as described elsewhere in the present disclosure (e.g., operation 620 in FIG. 6 and descriptions thereof).

In 750, the processing device 120 (e.g., the determination module 520) may determine motion information of the target subject between the first time point and the second time point based on the first position information and the second position information.

In some embodiments, the motion information of the target subject between the first time point and the second time point may include a moving velocity, a moving direction, a moving displacement, or the like, or any combination thereof. In some embodiments, the processing device 120 may determine the motion information of the target subject between the first time point and the second time point based on first coordinates of the target subject corresponding to the first time point, second coordinates of the target subject corresponding to the second time point, and a time difference between the first time point and the second time point. Merely by way of example, the motion information of the target subject may be represented by a motion vector of the target subject. For illustration purposes, the motion information of the target subject may be determined according to Equation (2):

$$d = (x_2 - x_1, y_2 - y_1, z_2 - z_1), \quad (2)$$

where $(x_1, y_1, z_1)$ refers to first coordinates of the target subject in the magnetic field coordinate system corresponding to a first time point; $(x_2, y_2, z_2)$ refers to second coordinates of the target subject in the magnetic field coordinate system corresponding to a second time point; and d refers to motion information of the target subject between the first time point and the second time point.

In some embodiments, the motion information may include posture information of the target subject (e.g., the patient), physiological motion information of the target subject (e.g., the patient), or the like, or any combination thereof. The posture information may reflect a posture motion of the target subject. The physiological motion information may reflect a motion of tissue or an organ that is caused or influenced by a physiological motion of the target subject. As used herein, a posture motion of the patient refers to a rigid motion of a portion (e.g., the head, a leg, a hand) of the patient. For example, the rigid motion may include a translational and/or rotational motion of the portion of the patient. Exemplary rigid motion may include the rotating or nodding of the head of the patient, legs motion, hands motion, or the like. The physiological motion may include a cardiac motion, a respiratory motion, a blood flow, a gastrointestinal motion, a skeletal muscle motion, a brain motion (e.g., a brain pulsation), or the like, or any combination thereof.

The position information of the target subject corresponding to a plurality of time points may reflect the motion of the target subject, and be used to determine the motion information of the target subject. In some embodiments, the motion information may include information relating to a corresponding motion of the target subject. The information relating to a physiological motion may include a motion rate, a motion amplitude (or displacement), a motion cycle, a motion phase, or the like, or any combination thereof. In some embodiments, the motion information may include an electrocardiogram (ECG) signal relating to the cardiac motion of the target subject, a respiratory signal relating to a respiratory motion of the target subject, a posture signal relating to the posture motion of the target subject, or the like. For example, the ECG signal may indicate cardiac cycle(s) of the target subject, as well as changes of the heart rate and/or cardiac motion amplitude over the cardiac cycle (s). A cardiac cycle may include a plurality of cardiac phases, such as systole (during which the left and right ventricles contract and eject blood into the aorta and pulmonary artery, respectively) and diastole (during which the ventricles are relaxed). As another example, the respiratory signal may indicate a respiratory cycle of the target subject, as well as a respiratory displacement, a respiratory rate, and/or a respiratory frequency, or the like. The respiratory cycle may include a plurality of respiratory phases, such as an inspiratory phase (during which the chest of the subject expands and air flows into the lungs) and an expiratory phase (during which the chest shrinks and air is pushed out of the lungs).

In some embodiments, the processing device 120 may determine the posture information based on position information corresponding to a plurality of time points (e.g., the first time point, the second time point). For example, the patient may be placed in a reference magnetic field (e.g., a main magnetic field and a plurality of gradient fields Gx, Gy, and Gz) in a medical system (e.g., an MRI system). A plurality of diamond NV center sensors may be disposed on a plurality of positions (e.g., the head, the neck, the hands, the feet, the legs, the arms) of the patient to determine position information of the plurality of positions corresponding to the plurality of time points. For each time point of the plurality of time points, the processing device 120 may determine a contour of the patient corresponding to the time point based on the position information of the plurality of positions corresponding to the time point. A contour of the patient may be formed by an edge of the surface of the patient. The processing device 120 may determine the posture information based on a plurality of contours of the patient corresponding to the plurality of time points. For example, the processing device 120 may determine a motion of the contour based on the plurality of contours of the patient corresponding to the plurality of time points. The processing device 120 may determine the posture information based on the motion of the contour. The motion of the contour may include a moving velocity of at least one position of a plurality of positions of the contour of the patient, a moving direction of at least one position of the plurality of positions of the contour of the patient, a moving displacement of at least one position of the plurality of positions of the contour of the patient between different time points, or the like, or any combination thereof.

In some embodiments, the processing device 120 may determine the physiological motion information (e.g., cardiac motion information, respiratory motion information) based on the position information of the patient corresponding to the plurality of time points. For example, the patient may be placed in a reference magnetic field (e.g., a main magnetic field) in a medical system (e.g., an MRI system). A plurality of diamond NV center sensors may be disposed on the scan region and/or a region (e.g., the chest, the abdomen, the neck) that may be significantly influenced by the physiological motion of the patient. The processing device 120 may extract the cardiac motion information and the respiratory motion information from the position information based on a frequency range of the respiratory motion and a frequency range of the cardiac motion according to a spectrum analysis. The frequency range of the cardiac motion and the frequency range of the cardiac motion may be manually set by a user of the medical system 100, or be determined by one or more components (e.g., the processing device 120) of the medical system 100 according to different situations. For a normal person, the frequency range of the cardiac motion may be higher than the frequency range of the cardiac motion. For example, the processing device 120 may generate filtered position information by performing a filtering operation on the position information to filter out a disturbed signal (e.g., the posture information). The processing device 120 may transform the filtered position information from the time domain to the frequency domain by performing a Fourier transformation on the filtered position information. The processing device 120 may then extract the cardiac motion information and the respiratory motion information from the filtered position information in the frequency domain based on the frequency range of the respiratory motion and the frequency range of the cardiac motion. The processing device 120 may further determine the cardiac motion information and the respiratory motion information in the time domain by performing an inverse Fourier transform on the cardiac motion information and the respiratory motion information in the frequency domain, respectively.

In 760, the processing device 120 (e.g., the control module 530) may cause a medical device to scan the target subject based on the motion information of the target subject.

In some embodiments, the processing device 120 may determine correction information based on the motion information of the target subject. In some embodiments, the medical device may be an MRI device. The correction information may include gradient correction information, radio frequency correction information, or the like, or any combination thereof.

The gradient correction information may be used for a gradient component of the MRI device to generate a gradient magnetic field. The gradient component may include gradient coils (e.g., the gradient coils 202). In some embodiments, the gradient correction information may include components of a gradient magnetic field along a first magnetic field direction (e.g., the X-axis direction of the coordinate system 160 as illustrated in FIG. 1), a second magnetic field direction (e.g., the Y-axis direction of the coordinate system 160 as illustrated in FIG. 1), and a third magnetic field direction (e.g., the Z-axis direction of the coordinate system 160 as illustrated in FIG. 1). For example, the gradient correction information may be determined according to Equation (3):

$$[G_X, G_Y, G_Z]^T = \text{RotMatrix\_log2phy\_Current} \times [G_{RO}, G_{PE}, G_{SS}]^T, \quad (3)$$

where $[G_X, G_Y, G_Z]$ refers to components of a gradient magnetic field along an X-axis direction, a Y-axis direction, and a Z-axis direction of a magnetic field coordinate system; $[G_X, G_Y, G_Z]^T$ refers to an inverse matrix of $[G_X, G_Y, G_Z]$; RotMatrix_log 2phy_Current refers to a rotation matrix between a logical coordinate system and the magnetic field coordinate system in an acquisition slice; $[G_{RO}, G_{PE}, G_{SS}]$ refers to components of the gradient magnetic field along a readout (RO) direction, a phase encoding (PE) direction, and a slice selection (SS) direction; and $[G_{RO}, G_{PE}, G_{SS}]^T$ refers to an inverse matrix of $[G_{RO}, G_{PE}, G_{SS}]$.

The RF correction information may be used for a radio frequency (RF) component of the MRI device to obtain an MRI signal of the target subject. The RF component may include an RF transmit component (e.g., RF transmit coils), an RF receiver component (e.g., RF receiver coils), or the like. In some embodiments, the RF correction information may include frequency correction information of the RF transmit component, phase correction information of the RF transmit component, frequency correction information of the RF receiver component, phase correction information of the RF receiver component, or the like, or any combination thereof. For example, the frequency correction information of the RF transmit component may be determined according to Equation (4):

$$\text{TX\_freq} = \gamma \times B_0 + \text{freq\_per\_ss} \times \text{Shift\_SS}, \quad (4)$$

where TX_freq refers to frequency correction information of an RF transmit component; y refers to a gyromagnetic ratio of a diamond NV center; $B_0$ refers to a magnetic field strength; freq_per_ss refers to a frequency variation per unit length along a slice selection direction in a logical coordinate system, which is a known quantity; and Shift_SS refers to a component of a displacement in an acquisition slice along the slice selection direction in the logical coordinate system.

The phase correction information of the RF transmit component may be determined according to Equation (5):

$$\text{TX\_phase} = -\gamma \times GSS \times \text{Duration\_RF} \times \\ \text{AsymmetricFactor\_RF} \times \text{Shift\_SS} + \text{phase\_RF}, \quad (5)$$

where TX_phase refers to phase correction information of an RF transmit component; GSS refers to a component of a gradient magnetic field along a slice selection direction in a logical coordinate system; Duration_RF refers to a duration of an RF pulse; AsymmetricFactor_RF refers to an asymmetric factor of the RF pulse; and phase_RF refers to a designated phase.

The frequency correction information of the RF receiver component may be determined according to Equation (6):

$$\text{RX\_freq} = \gamma \times B_0 + \text{freq\_per\_ro} \times \text{Shift\_RO}, \quad (6)$$

where X_freq refers to frequency correction information of an RF receiver component; req_per_ro refers to a frequency variation per unit length along a readout direction in a logical coordinate system, which is a known quantity; and Shift_RO refers to a component of a displacement in an acquisition slice along the readout direction in the logical coordinate system.

The phase correction information of the RF receiver component may be determined according to Equation (7):

$$RX\_phase = phase\_per\_pe \times Shift\_PE + phase\_per\_SS \times Shift\_SS, \quad (7)$$

where RX_phase refers to phase correction information of an RF receiver component; phase_per_pe refers to a phase variation per unit length along a phase encoding direction in a logical coordinate system, which is a known quantity; phase_per_SS refers to a phase variation per unit length along a slice phase encoding (SPE) direction in the logical coordinate system, which is a known quantity; and Shift_SS refers to a component of a displacement in an acquisition slice along the slice selection direction in the logical coordinate system.

Further, the processing device 120 may obtain an MRI image of the target subject by causing the MRI device to scan the target subject based on the correction information. The gradient correction information may be transmitted to the gradient component. The radio frequency correction information may be transmitted to the RF component. In some embodiments, the processing device 120 may cause the gradient component of the MRI device to generate the gradient magnetic field based on the gradient correction information. The processing device 120 may cause the RF component of the MRI device to obtain an MRI signal of the target subject based on the radio frequency correction information. The processing device 120 may obtain spatial encoding information based on the gradient magnetic field. For example, the processing device 120 may perform a spatial encoding on the MRI signal based on the gradient magnetic field to obtain the spatial encoding information. The processing device 120 may obtain the MRI image of the target subject by processing the MRI signal based on the spatial encoding information. For example, the processing device 120 may perform a Fourier transform on the MRI signal based on the spatial encoding information to obtain the MRI image of the target subject.

According to some embodiments of the present disclosure, the gradient correction information and the radio frequency correction information may be determined based on the motion information of the target subject. The gradient magnetic field may be generated based on the gradient correction information, and the MRI signal of the target subject may be obtained based on the radio frequency correction information. The relative spatial position of the target subject in the gradient magnetic field before and after the movement of the target subject may be the same. By causing the MRI device to scan the target subject based on the correction information, motion artifacts in the MRI image reconstructed based on MRI signals detected in the MRI scan may be reduced, and the quality of the MRI image may be improved.

In some embodiments, the processing device 120 may transmit the motion information of the target subject to a sequence control unit of the MRI device. A label indicating the motion information may be added in a scan sequence based on the motion information. When the scan sequence is run to the label, the sequence control unit may determine the gradient correction information and the radio frequency correction information based on the motion information. The processing device 120 may cause the MRI device to scan the target subject based on the gradient correction information and the radio frequency correction information. The obtaining of the motion information of the target subject and the acquisition of the MRI data may be performed independently and simultaneously.

In some embodiments, the processing device 120 may generate an image (e.g., an MRI image) of the subject based on the scan (e.g., an MRI scan). The processing device 120 may perform an artifact correction on the image of the subject based on the motion information. For example, the motion information may include information regarding a respiratory signal. The processing device 120 may utilize a respiratory compensation technique, such as a respiratory ordered phase encoding (ROPE) technique, a centrally ordered phase encoding (COPE) technique, a hybrid ordered phase encoding (HOPE), or the like, or any combination thereof in the MRI image reconstruction. For example, based on information regarding a respiratory signal, the processing device 120 may apply a same phase encoding or similar phase encodings to MRI signals corresponding to a same respiratory phase or similar respiratory phases in the MRI image reconstruction. In the resulting MRI image, motion artifacts may be eliminated or partially eliminated.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operation 730 may be performed before operation 720. As another example, operation 730 and operation 720 may be performed simultaneously. As still another example, operation 730 and operation 740 may be performed simultaneously.

In some embodiments, in response to determining that the motion information of the target subject is detected during an operation, e.g., a scan of the target subject, the processing device 120 may cause the medical device to terminate or pause the operation. Thus, the quality of the operation, e.g., assessed based on the quality of an image generated based on the scan, may be improved and the operation time may be saved.

In some embodiments, the processing device 120 may obtain, via the plurality of diamond NV center sensors, first magnetic field information $B_1$ of the target subject corresponding to the first time point. The processing device 120 may determine first position information $P_1$ of the target subject corresponding to the first time point based on the first magnetic field information $B_1$ and the magnetic field distribution information of the reference magnetic field. As the second time point, the processing device 120 may obtain magnetic field information variation $B_x$ of the target subject between the first time point and the second time point. That is, the second magnetic field information of the target subject corresponding to the second time point may be $B_2=B_1+B_x$. The processing device 120 may determine second position information $P_2$ of the target subject corresponding to the second time point based on the second magnetic field information $B_2$ and the magnetic field distribution information of the reference magnetic field. The processing device 120 may determine the motion information based on the first position information $P_1$ and the second position information $P_2$.

Figure 8:
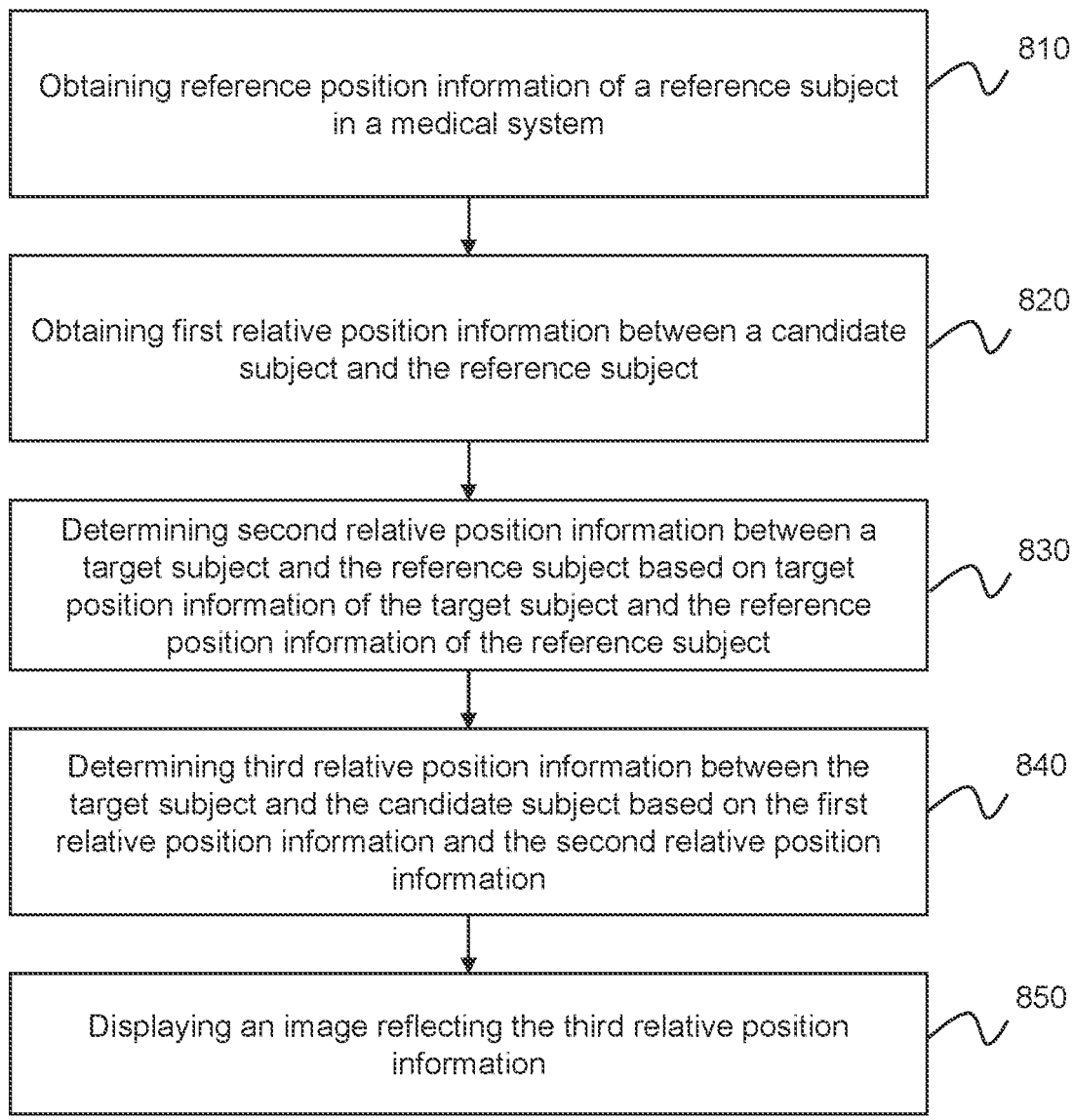
FIG. 8 is a flowchart illustrating an exemplary process for displaying an image reflecting a relative position information between a target subject and a candidate subject according to some embodiments of the present disclosure.

FIG. 8 is a flowchart illustrating an exemplary process for displaying an image reflecting a relative position information between a target subject and a candidate subject according to some embodiments of the present disclosure. In some embodiments, process 800 may be implemented in the medical system 100 or the medical system 200 illustrated in FIG. 1. For example, the process 800 may be stored in the storage device 130 and/or the storage (e.g., the storage device 320, the storage 490) as a form of instructions, and invoked and/or executed by the processing device 120 (e.g., the processor 222 as illustrated in FIG. 2, the processor 310 of the computing device 300 as illustrated in FIG. 3, the CPU 440 of the mobile device 400 as illustrated in FIG. 4). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

In 810, the processing device 120 (e.g., the obtaining module 510) may obtain reference position information of a reference subject in a medical system.

In some embodiments, the reference subject may remain stationary in the medical system 100 during a medical operation (e.g., a puncture surgery, a minimally invasive surgery). For example, the reference subject may be a marker mounted on one or more components (e.g., a scanning table, a gantry) of a medical device (e.g., an MRI device). The reference position information of the reference subject may include reference coordinates of the reference subject in a reference coordinate system. The reference coordinate system may be similar to the coordinate system 160 as shown in FIGS. 1 and 2. For illustration purposes, an origin of the reference coordinate system may be the position of the reference subject, a reference X-axis direction of the reference coordinate system may be parallel to the X-axis direction of the coordinate system 160, a reference Y-axis direction of the reference coordinate system may be parallel to the Y-axis direction of the coordinate system 160, and a reference Z-axis direction of the reference coordinate system may be parallel to the Z-axis direction of the coordinate system 160. In some embodiments, the reference position information of the reference subject may be determined by one or more components of the medical system 100, or manually set by a user of the medical system 100 according to different situations. For example, the user may input the reference coordinates of the reference subject.

In 820, the processing device 120 (e.g., the obtaining module 510) may obtain first relative position information between a candidate subject and the reference subject.

In some embodiments, the candidate subject may be a patient to be scanned by the medical device. The first relative position information between the candidate subject and the reference subject may indicate a position of the candidate subject relative to the reference subject in the reference coordinate system. In some embodiments, the processing device 120 may obtain the first relative position information based on an image of the candidate subject and the reference subject. The image may indicate a position of the candidate subject relative to the reference subject in an image coordinate system. The image may be obtained by an image capturing device (e.g., a camera), a medical device, or the like. For example, the processing device 120 may obtain an image (e.g., an MRI image) of the candidate subject and the reference subject. The processing device 120 may determine reference coordinates of the candidate subject in the reference coordinate system based on image coordinates of the candidate subject in the image coordinate system and a transformation relationship between the image coordinate system and the reference coordinate system. The transformation relationship between the image coordinate system and the reference coordinate system may be determined based on image coordinates of the reference subject in the image coordinate system and the reference coordinates of the of the reference subject in the reference coordinate system. For illustration purposes, assuming that a transformation relationship between the image coordinate system and the reference coordinate system is M, and the image coordinates of the candidate subject is (X, Y, Z), the processing device 120 may determine that the reference coordinates of the candidate subject in the reference coordinate system is (X, Y, Z)*M.

In 830, the processing device 120 (e.g., the determination module 520) may determine second relative position information between a target subject and the reference subject based on target position information of the target subject and the reference position information of the reference subject.

In some embodiments, the target subject may be an operating element (e.g., a puncture needle). The target position information of the operating element may be determined based on target magnetic field information of the operating element obtained via at least one diamond NV center sensor. More descriptions for determining the target position information of the target subject may be found elsewhere in the present disclosure (e.g., FIG. 6 and descriptions thereof).

The second relative position information between the target subject and the reference subject may indicate a position of the target subject relative to the reference subject in the reference coordinate system. In some embodiments, the processing device 120 may determine the second relative position information between the target subject and the reference subject based on the target position information of the target subject and the reference position information of the reference subject. For example, the processing device 120 may determine reference coordinates of the target subject in the reference coordinate system based on magnetic field coordinates of the target subject in the magnetic field coordinate system and a coordinate transformation relationship between the magnetic field coordinate system and the reference coordinate system. For illustration purposes, assuming that a transformation relationship between the magnetic field coordinate system and the reference coordinate system is N, and the magnetic field coordinates of the target subject is (X, Y, Z), the processing device 120 may determine that the reference coordinates of the target subject in the reference coordinate system is (X, Y, Z)*N. The processing device 120 may determine the second relative position information based on the reference coordinates of the target subject and the reference coordinates of the reference subject in the reference coordinate system.

In 840, the processing device 120 (e.g., the determination module 520) may determine third relative position information between the target subject and the candidate subject based on the first relative position information and the second relative position information.

The third relative position information between the target subject and the candidate subject may indicate a position of the target subject relative to the candidate subject in the reference coordinate system. In some embodiments, the processing device 120 may determine the third relative position information based on the reference coordinates of the target subject and the reference coordinates of the candidate subject in the reference coordinate system. According to some embodiments of the present disclosure, the relative position information between the target subject and the candidate subject may be determined using the reference subject fixed in the medical system 100, a positioning error of the target subject caused by the movement of the candidate subject may be avoided, and the accuracy and speed of positioning the target subject may be improved.

In 850, the processing device 120 (e.g., the control module 530) may display an image reflecting the third relative position information.

For example, the processing device 120 may generate the image reflecting the third relative position information, and transmit the image to a terminal device (e.g., the terminal 140) for display. A user (e.g., an operator, a doctor) may view the image on the terminal device (e.g., the terminal 140). Accordingly, the user may perform the medical operation with the guidance of the image, which may improve the efficiency and accuracy of the medical operation.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 120 determine the relative position information between the target subject and the candidate subject based on first target position information of the target subject and second target position information of the candidate subject. For example, at least one first diamond NV center sensor may be configured on the target subject to obtain first target magnetic field information of the target subject. At least one second diamond NV center sensor may be configured on the candidate subject to obtain second target magnetic field information of the candidate subject. The first target position information of the target subject (e.g., coordinates of the target subject in the magnetic field coordinate system) may be determined based on the first target magnetic field information of the target subject. The second target position information of the candidate subject (e.g., coordinates of the candidate subject in the magnetic field coordinate system) may be determined based on the second target magnetic field information of the candidate subject. The relative position information between the target subject and the candidate subject may be determined based on first target position information of the target subject and second target position information of the candidate subject.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A method implemented on a computing device having at least one processor and at least one storage device, the method comprising:

obtaining, via a plurality of sensors, real-time target magnetic field information of a target subject, wherein the plurality of sensors are configured on the target subject, the plurality of sensors include a plurality of diamond nitrogen-vacancy (NV) center sensors, the target subject is located in a reference magnetic field in a magnetic resonance imaging (MRI) system, the real-time target magnetic field information refers to a magnetic field strength vector corresponding to a magnetic field direction in a magnetic field coordinate system of the reference magnetic field, the reference magnetic field includes a main magnetic field and a plurality of gradient magnetic fields generated by the MRI system; and determining real-time target position information of the target subject based on the real-time target magnetic field information of the target subject and magnetic field distribution information of the reference magnetic field in the MRI system, the magnetic field distribution information of the reference magnetic field reflecting a relationship between target position information of the target subject in the reference magnetic field and target magnetic field information of the target subject in the reference magnetic field, the real-time target magnetic field information of the target subject being the target magnetic field information of the target subject obtained in real time, and the real-time target position information of the target subject being the target position information of the target subject determined based on the real-time target magnetic field information of the target subject, wherein the real-time target magnetic field information of the target subject is obtained by:

for each pair of at least one pair of magnetic resonance peaks of a diamond NV center in the diamond NV center sensor, obtaining candidate magnetic field information related to a corresponding crystal axis direction in a crystal coordinate system of the diamond NV center, the candidate magnetic field information referring to a magnetic field strength vector corresponding to the corresponding crystal axis direction in the crystal coordinate system of the diamond NV center; and determining the real-time target magnetic field information based on the candidate magnetic field information of each pair of the at least one pair of magnetic resonance peaks of the diamond NV center and a coordinate transformation relationship between the crystal coordinate system of the diamond NV center and the magnetic field coordinate system of the reference magnetic field.

2. The method of claim 1, wherein the obtaining the candidate magnetic field information comprises:

obtaining information of the at least one pair of magnetic resonance peaks of the diamond NV center in the diamond NV center sensor, the information of the at least one pair of magnetic resonance peaks including at least one of a probe microwave frequency of each magnetic resonance peak, a fluorescence intensity of each magnetic resonance peak, or a linewidth of each magnetic resonance peak, wherein the at least one pair of magnetic resonance peaks of the diamond NV center is obtained by splitting a total magnetic resonance peak of the diamond NV center via the reference magnetic field, and each pair of the at least one pair of magnetic resonance peaks corresponds to the corresponding crystal axis direction of the diamond NV center; and for each pair of the at least one pair of magnetic resonance peaks of the diamond NV center, determining the candidate magnetic field information related to the corresponding crystal axis direction of the diamond NV center based on the information of the pair of magnetic resonance peaks.

3. The method of claim 1, wherein the target subject is a scan region of a patient, and the obtaining, via the plurality of sensors, the real-time target magnetic field information of the target subject comprises:

obtaining, via the plurality of sensors, first magnetic field information of the target subject corresponding to a first time point; and obtaining, via the plurality of sensors, second magnetic field information of the target subject corresponding to a second time point, wherein the second time point is different from the first time point.

4. The method of claim 1, wherein the target subject is an operating element, and the method further comprising:

obtaining reference position information of a reference subject in the medical system;

obtaining first relative position information between a candidate subject and the reference subject;

determining second relative position information between the target subject and the reference subject based on the real-time target position information of the target subject and the reference position information of the reference subject; and determining third relative position information between the target subject and the candidate subject based on the first relative position information and the second relative position information.

5. The method of claim 4, further comprising:

displaying an image reflecting the third relative position information.

6. The method of claim 1, wherein the reference magnetic field includes the main magnetic field generated by the MRI system, and the real-time target magnetic field information of the target subject located in the main magnetic field is used for determining physiological motion information of the target subject, the physiological motion information reflecting a motion of tissue or an organ of the target subject that is caused or influenced by a physiological motion of the target subject.

7. The method of claim 1, wherein the real-time target magnetic field information of the target subject located in the main magnetic field and the plurality of gradient magnetic fields is used for determining posture information of the target subject, the posture information reflecting a posture motion of the target subject, wherein the posture information of the target subject is determined by:
  determining second position information of a plurality of positions of the target subject corresponding to the plurality of time points, a plurality of diamond NV center sensors being disposed on the plurality of positions of the target subject;
  for each time point of the plurality of time points, determining a contour of the target subject corresponding to the time point based on the position information of the plurality of positions corresponding to the time point, the contour of the target subject being formed by an edge of a surface of the target subject; and
  determining the posture information of the target subject based on the plurality of contours of the target subject corresponding to the plurality of time points.

8. The method of claim 3, wherein the real-time target position information of the target subject includes motion information of the target subject between the first time point and the second time point, and the determining real-time target position information of the target subject based on the real-time target magnetic field information of the target subject and magnetic field distribution information of the reference magnetic field in the medical system comprises:
  determining first position information of the target subject corresponding to the first time point based on the first magnetic field information of the target subject and the magnetic field distribution information of the reference magnetic field;
  determining second position information of the target subject corresponding to the second time point based on the second magnetic field information of the target subject and the magnetic field distribution information of the reference magnetic field; and
  determining the motion information of the target subject between the first time point and the second time point based on the first position information and the second position information.

9. The method of claim 8, further comprising:
  causing an MRI device in the MRI system to scan the target subject based on the motion information of the target subject.

10. The method of claim 9, wherein the causing the MRI device in the MRI system to scan the target subject based on the motion information of the target subject comprises:
  determining correction information based on the motion information of the target subject; and
  obtaining an MRI image of the target subject by causing the MRI device to scan the target subject based on the correction information.

11. The method of claim 10, wherein the correction information includes at least one of gradient correction information or radio frequency correction information.

12. The method of claim 11, wherein the obtaining the MRI image of the target subject by causing the MRI device to scan the target subject based on the correction information comprises:

causing a gradient component of the MRI device to generate a corrected gradient magnetic field based on the gradient correction information;
causing a radio frequency component of the MRI device to obtain an MRI signal of the target subject based on the radio frequency correction information;
obtaining spatial encoding information based on the corrected gradient magnetic field; and
obtaining the MRI image of the target subject by processing the MRI signal based on the spatial encoding information.

13. A magnetic resonance imaging (MRI) system, comprising:
  at least one storage device storing a set of instructions; and
  at least one processor in communication with the at least one storage device, when executing the stored set of instructions, the at least one processor causes the system to perform operations including:
    obtaining, via a plurality of sensors, real-time target magnetic field information of a target subject, wherein the plurality of sensors are configured on the target subject, the plurality of sensors include a diamond nitrogen-vacancy (NV) center sensor, the target subject is located in a reference magnetic field in the MRI system, the real-time target magnetic field information refers to a magnetic field strength vector corresponding to a magnetic field direction in a magnetic field coordinate system of the reference magnetic field, the reference magnetic field includes a main magnetic field and a plurality of gradient magnetic fields generated by the MRI system, the real-time target magnetic field information of the target subject located in the main magnetic field and the plurality of gradient magnetic fields being used for determining posture information of the target subject, the posture information reflecting a posture motion of the target subject; and
    determining real-time target position information of the target subject based on the real-time target magnetic field information of the target subject and magnetic field distribution information of the reference magnetic field in the MRI system, the magnetic field distribution information of the reference magnetic field reflecting a relationship between target position information of the target subject in the reference magnetic field and target magnetic field information of the target subject in the reference magnetic field, the real-time target magnetic field information of the target subject being the target magnetic field information of the target subject obtained in real time, and the real-time target position information of the target subject being the target position information of the target subject determined based on the real-time target magnetic field information of the target subject, wherein the real-time target magnetic field information of the target subject is obtained by:
      for each pair of at least one pair of magnetic resonance peaks of a diamond NV center in the diamond NV center sensor, obtaining candidate magnetic field information related to a corresponding crystal axis direction in a crystal coordinate system of the diamond NV center, the candidate magnetic field information referring to a magnetic field strength vector corresponding to the corresponding crystal axis direction in the crystal coordinate system of the diamond NV center; and determining the real-time target magnetic field information based on the candidate magnetic field information of each pair of the at least one pair of magnetic resonance peaks of the diamond NV center and a coordinate transformation relationship between the crystal coordinate system of the diamond NV center and the magnetic field coordinate system of the reference magnetic field.

14. The system of claim 13, wherein the obtaining the candidate magnetic field information comprises:

obtaining information of the at least one pair of magnetic resonance peaks of the diamond NV center in the diamond NV center sensor, the information of the at least one pair of magnetic resonance peaks including at least one of a probe microwave frequency of each magnetic resonance peak, a fluorescence intensity of each magnetic resonance peak, or a linewidth of each magnetic resonance peak, wherein the at least one pair of magnetic resonance peaks of the diamond NV center is obtained by splitting a total magnetic resonance peak of the diamond NV center via the reference magnetic field, and each pair of the at least one pair of magnetic resonance peaks corresponds to the crystal axis direction of the diamond NV center; and for each pair of the at least one pair of magnetic resonance peaks of the diamond NV center, determining the candidate magnetic field information related to the corresponding crystal axis direction of the diamond NV center based on the information of the pair of magnetic resonance peaks.

15. The system of claim 13, wherein the target subject is a scan region of a patient, and the obtaining, via the plurality of sensors, the real-time target magnetic field information of the target subject comprises:

obtaining, via the plurality of sensors, first magnetic field information of the target subject corresponding to a first time point; and obtaining, via the plurality of sensors, second magnetic field information of the target subject corresponding to a second time point, wherein the second time point is different from the first time point.

16. The system of claim 15, wherein the real-time target position information of the target subject includes motion information of the target subject between the first time point and the second time point, and the determining real-time target position information of the target subject based on the real-time target magnetic field information of the target subject and magnetic field distribution information of the reference magnetic field in the medical system comprises:

determining first position information of the target subject corresponding to the first time point based on the first magnetic field information of the target subject and the magnetic field distribution information of the reference magnetic field;

determining second position information of the target subject corresponding to the second time point based on the second magnetic field information of the target subject and the magnetic field distribution information of the reference magnetic field; and determining the motion information of the target subject between the first time point and the second time point based on the first position information and the second position information.

17. The system of claim 16, wherein the at least one processor further causes the system to perform operations including:

causing an MRI device in the MRI system to scan the target subject based on the motion information of the target subject.

18. The system of claim 17, wherein the causing the MRI device in the MRI system to scan the target subject based on the motion information of the target subject comprises:

determining correction information based on the motion information of the target subject; and obtaining an MRI image of the target subject by causing the MRI device to scan the target subject based on the correction information.

19. A non-transitory computer readable medium, comprising at least one set of instructions, wherein when executed by at least one processor of a computing device, the at least one set of instructions cause the at least one processor to effectuate a method comprising:

obtaining, via a plurality of sensors, real-time target magnetic field information of a target subject, wherein the plurality of sensors are configured on the target subject, the plurality of sensors include a diamond nitrogen-vacancy (NV) center sensor, the target subject is located in a reference magnetic field in a magnetic resonance imaging (MRI) system, the real-time target magnetic field information refers to a magnetic field strength vector corresponding to a magnetic field direction in a magnetic field coordinate system of the reference magnetic field, the reference magnetic field includes a main magnetic field and a plurality of gradient magnetic fields generated by the MRI system, the real-time target magnetic field information of the target subject located in the main magnetic field and the plurality of gradient magnetic fields being used for determining posture information of the target subject, the posture information reflecting a posture motion of the target subject; and determining real-time target position information of the target subject based on the real-time target magnetic field information of the target subject and magnetic field distribution information of the reference magnetic field in the MRI system, the magnetic field distribution information of the reference magnetic field reflecting a relationship between target position information of the target subject in the reference magnetic field and target magnetic field information of the target subject in the reference magnetic field, the real-time target magnetic field information of the target subject being the target magnetic field information of the target subject obtained in real time, and the real-time target position information of the target subject being the target position information of the target subject determined based on the real-time target magnetic field information of the target subject, wherein the real-time target magnetic field information of the target subject is obtained by:

for each pair of at least one pair of magnetic resonance peaks of a diamond NV center in the diamond NV center sensor, obtaining candidate magnetic field information related to a corresponding crystal axis direction in a crystal coordinate system of the diamond NV center, the candidate magnetic field information referring to a magnetic field strength vector corresponding to the corresponding crystal axis direction in the crystal coordinate system of the diamond NV center; and determining the real-time target magnetic field information based on the candidate magnetic field information of each pair of the at least one pair of magnetic resonance peaks of the diamond NV center and a coordinate transformation relationship between the crystal coordinate system of the diamond NV center and the magnetic field coordinate system of the reference magnetic field.

* * * * *